(12) United States Patent
Chava et al.

(10) Patent No.: US 10,301,321 B2
(45) Date of Patent: May 28, 2019

(54) PROCESS FOR THE PREPARATION OF DOLUTEGRAVIR AND PHARMACEUTICALLY ACCEPTABLE SALTS THEREOF

(71) Applicant: Laurus Labs Limited, Andhra Pradesh (IN)

(72) Inventors: Satyanarayana Chava, Hyderabad (IN); Seeta Rama Anjaneyulu Gorantla, Hyderabad (IN); Venkata Lakshmi Narasimha Dammalapati, Hyderabad (IN); Mani Bushan Kotala, Hyderabad (IN); Ravindra Aduri, Hyderabad (IN)

(73) Assignee: LAURUS LABS LIMITED, Hyderbad (IN)

( * ) Notice: Subject to any disclaimer, the term of this patent is extended or adjusted under 35 U.S.C. 154(b) by 0 days.

(21) Appl. No.: 15/809,151

(22) Filed: Nov. 10, 2017

(65) Prior Publication Data

US 2018/0155364 A1  Jun. 7, 2018

Related U.S. Application Data

(62) Division of application No. 15/113,080, filed as application No. PCT/IB2015/000048 on Jan. 20, 2015, now Pat. No. 9,856,271.

(30) Foreign Application Priority Data

Jan. 21, 2014 (IN) .............................. 247/CHE/2014

(51) Int. Cl.
| | | |
|---|---|---|
| *C07D 498/14* | (2006.01) | |
| *C07D 213/82* | (2006.01) | |
| *C07D 317/30* | (2006.01) | |
| *C07D 319/06* | (2006.01) | |
| *C07C 235/80* | (2006.01) | |
| *C07C 237/16* | (2006.01) | |

(52) U.S. Cl.
CPC .......... *C07D 498/14* (2013.01); *C07C 235/80* (2013.01); *C07C 237/16* (2013.01); *C07D 213/82* (2013.01); *C07D 317/30* (2013.01); *C07D 319/06* (2013.01); *C07B 2200/13* (2013.01)

(58) Field of Classification Search
CPC ..................................................... C07D 498/14
USPC ........................................................... 544/95
See application file for complete search history.

(56) References Cited

FOREIGN PATENT DOCUMENTS

| WO | WO-2015177537 A1 | 11/2015 |
| WO | WO-2015195656 A2 | 12/2015 |
| WO | WO-2016092527 A1 | 6/2016 |

*Primary Examiner* — Kahsay Habte
(74) *Attorney, Agent, or Firm* — Blank Rome LLP

(57) ABSTRACT

The present invention relates to a novel process for the preparation of dolutegravir and pharmaceutically acceptable salts thereof using novel intermediates.

21 Claims, 8 Drawing Sheets

PROCESS FOR THE PREPARATION OF DOLUTEGRAVIR AND PHARMACEUTICALLY ACCEPTABLE SALTS THEREOF

CROSS-REFERENCE TO RELATED APPLICATIONS

This application is a divisional of and claims the benefit of U.S. application Ser. No. 15/113,080, filed Jul. 21, 2016, which is a national phase application of and claims the benefit of International Application PCT/IB2015/000048, filed on Jan. 20, 2015, which is based on and claims the benefit of Indian Provisional Application No. 247/CHE/2014, filed Jan. 21, 2014, entitled "Novel process for the preparation of Dolutegravir and pharmaceutically acceptable salts thereof," the contents and disclosures of which are incorporated by reference herein.

FIELD OF THE INVENTION

The present invention relates to a novel process for the preparation of dolutegravir and pharmaceutically acceptable salts thereof. The present invention also encompasses the novel intermediates used therein.

BACKGROUND OF THE INVENTION

Dolutegravir is chemically known as (4R,12aS)-9-{[(2,4-difluorophenyl)methyl] carbamoyl}-4-methyl-6,8-dioxo-3,4,6,8,12,12a-hexahydro-2H-pyrido[1',2':4,5]pyrazino [2,1-b][1,3]oxazin-7-olate, having the following Formula I:

Formula I

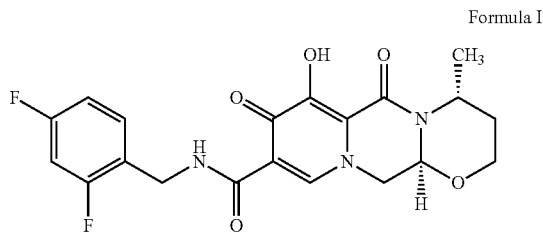 [SMILES: C[C@@H]1CCO[C@H]2Cn3cc(C(=O)NCc4ccc(F)cc4F)c(=O)c(O)c3C(=O)N12]

Dolutegravir (DTG, GSK1349572) is an integrase inhibitor being developed for the treatment of human immunodeficiency virus (HIV)-1 infection. Sodium salt of dolutegravir was recently approved by FDA and marketed under the brand name of TIVICAY by ViiV Healthcare and manufactured by GlaxoSmithKline. TIVICAY is administered orally as a tablet of 50 mg strength.

Tivicay is a human immunodeficiency virus type 1 (HIV-1) integrase strand transfer inhibitor (INSTI) indicated in combination with other antiretroviral agents for the treatment of HIV-1 infection.

Dolutegravir and a process for its preparation was first described in U.S. Pat. No. 8,129,385 and the disclosed process of dolutegravir involves 16 steps which is schematically represented as follows:

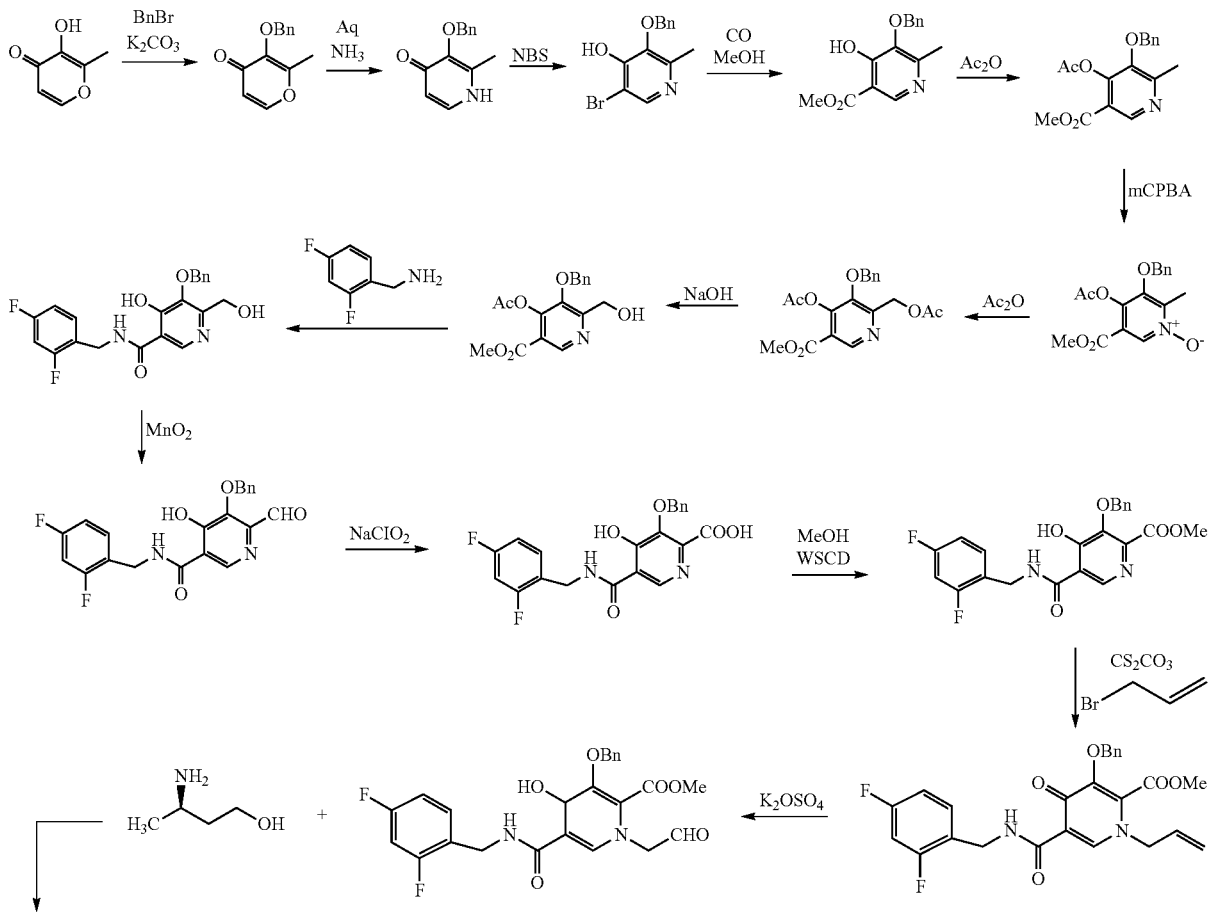

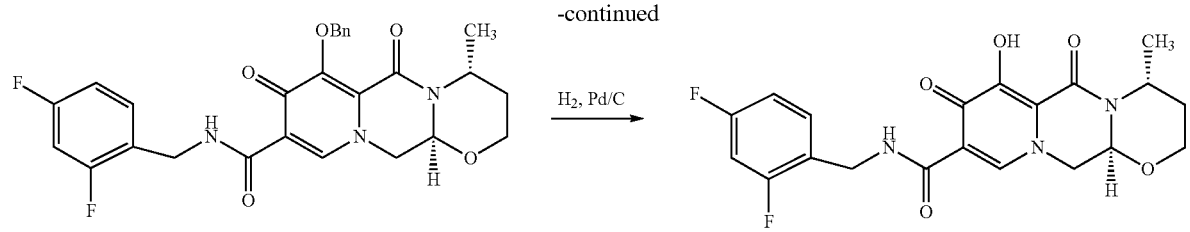
U.S. Pat. No. 8,217,034 ("the '034 patent") discloses the preparation of Dolutegravir. The process disclosed in the '034 patent is schematically represented as follows:

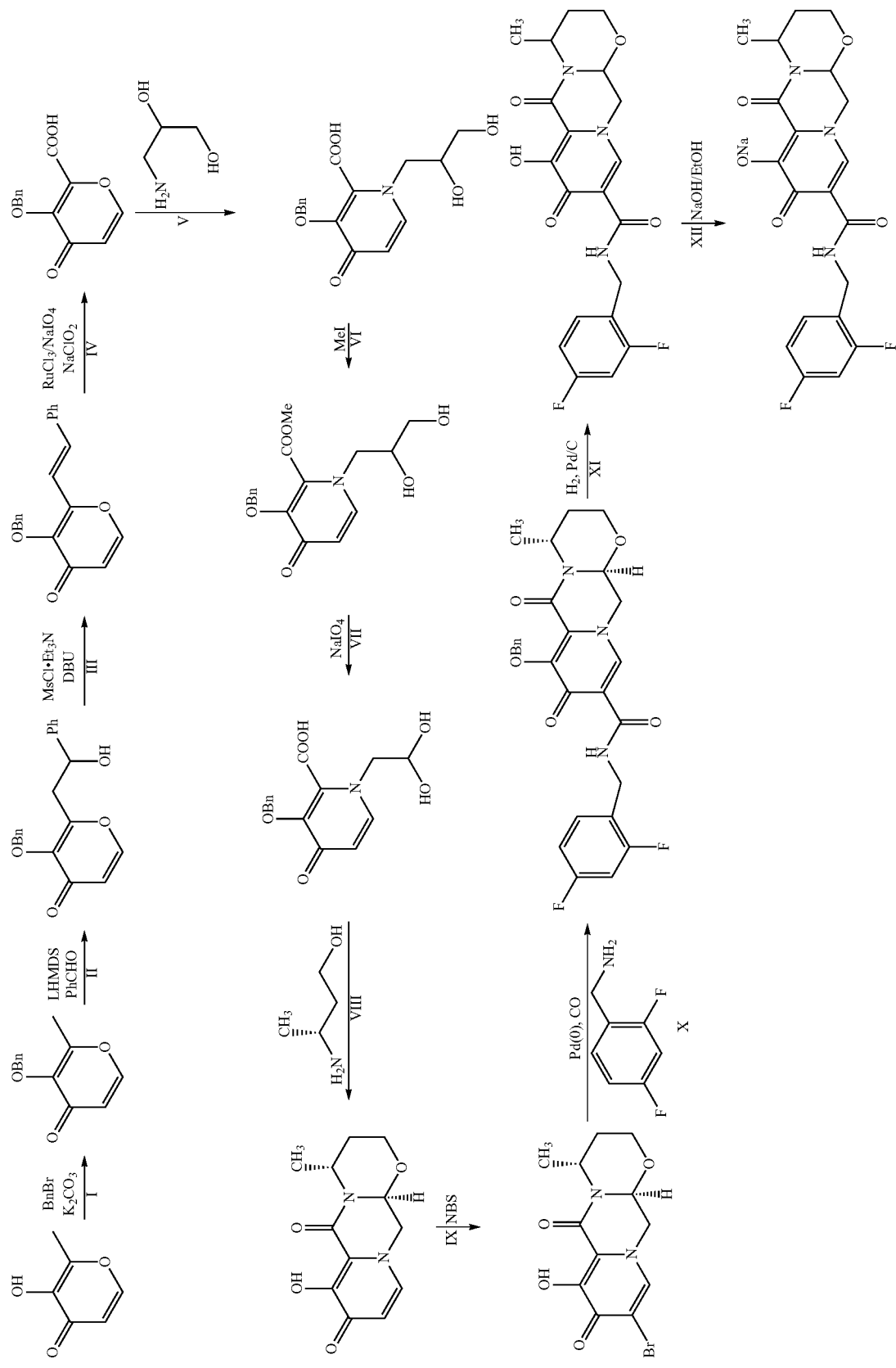

U.S. Pat. No. 8,552,187 ("the '187 patent") discloses the preparation of Dolutegravir intermediate. The process disclosed in the '187 patent is schematically represented as follows:

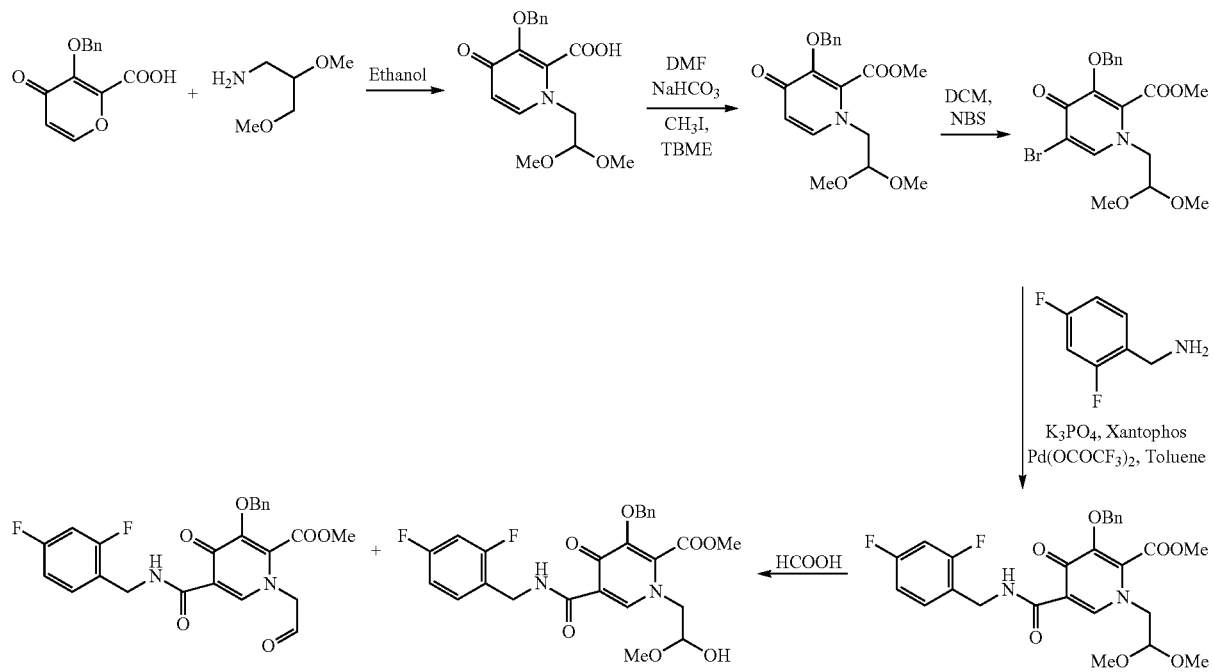

PCT Publication No. WO 2011/119566 ("the '566 publication") discloses the preparation of Dolutegravir. The process disclosed in the '566 publication is schematically represented as follows:

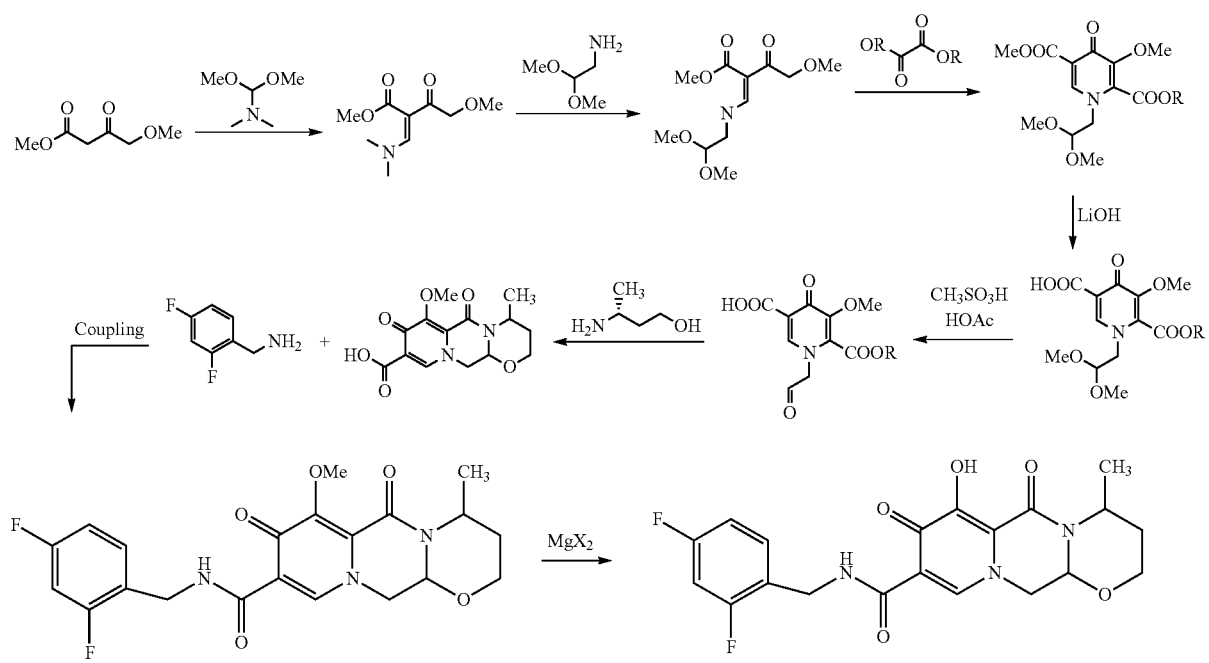

PCT Publication No. WO 2012/018065 ("the '065 publication") discloses the different preparation methods to prepare Dolutegravir. The preparation methods disclosed in the '065 publication is schematically represented as follows:

Preparation Method 1:
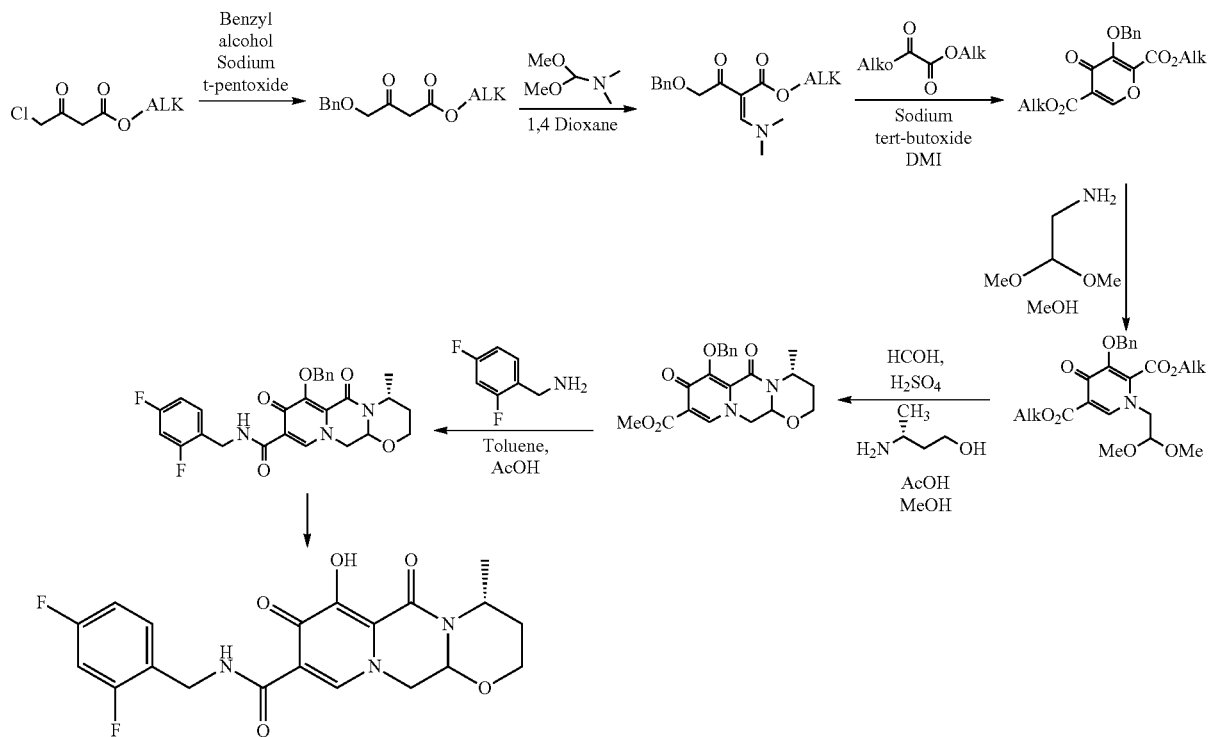
Preparation Method 2:
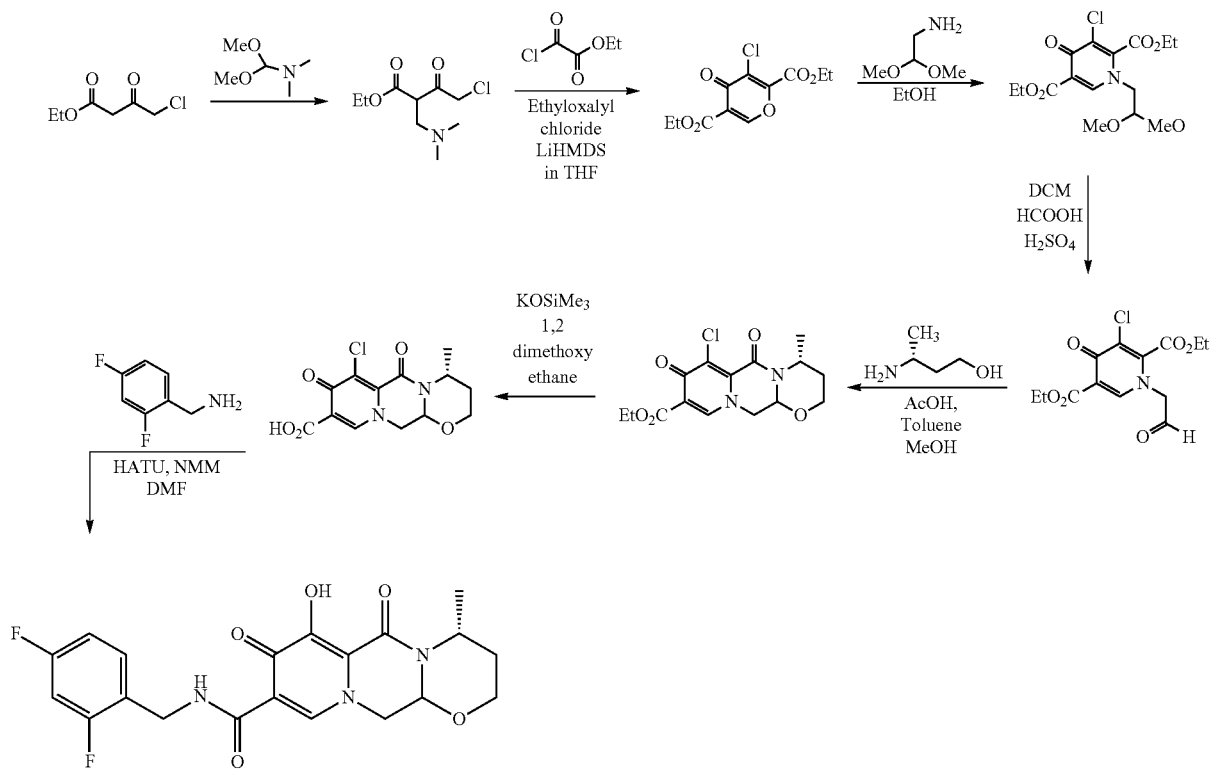

Preparation Method 3:

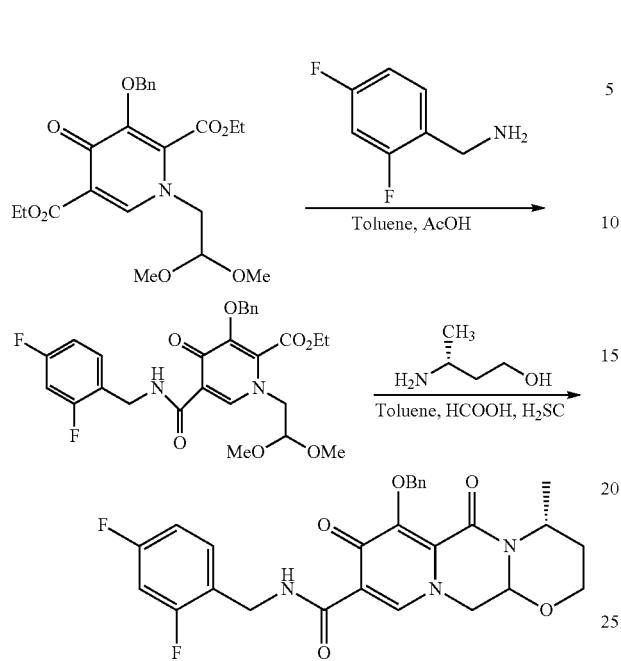

Indian patent publication 1361/CHE/2013 discloses a process for the preparation of dolutegravir, which involves the reaction 5-methoxy-6-(methoxycarbonyl)-4-oxo-1(2-oxoethyl)-1,4-dihydropyridine-3-carboxylic acid with tartarate salt of (R)-3-amino-1-butanol in presence of sodium acetate in acetonitrile to provide (4R, 12aS)-7-methoxy-4-methyl-6,8-dioxo-3,4,6,8,12,12a-hexahydro2H-pyrido[1',2': 4,5]pyrazino[2,1-b][1,3]oxazine-9-carboxylicacid, which on condensation with 2,4-difluorobenzylamine in presence of pivaloyl chloride, triethylamine in methylene chloride to provide (4R, 12aS)-N-(2,4-difluorobenzyl)-7-methoxy-4-methyl-6,8-dioxo-3,4,6,8,12,12a-hexahydro-2H-pyrido[1', 2':4,5]pyrazino [2,1-b][1,3]oxazine-9-carboxamide, which on reaction with lithium bromide in isopropyl alcohol provides dolutegravir.

PCT Publication No. WO 2015001572 ("the '572 publication") discloses the two different method for the preparation of dolutegravir intermediate i.e., methyl 3-(benzyloxy)-5-(2,4-difluorobenzylcarbamoyl)-4-oxo-1-(2-oxoethyl)-1,4-dihydropyiridine-2-carboxylate. The preparation methods disclosed in the '572 publication is schematically represented as follows:

Method-1:

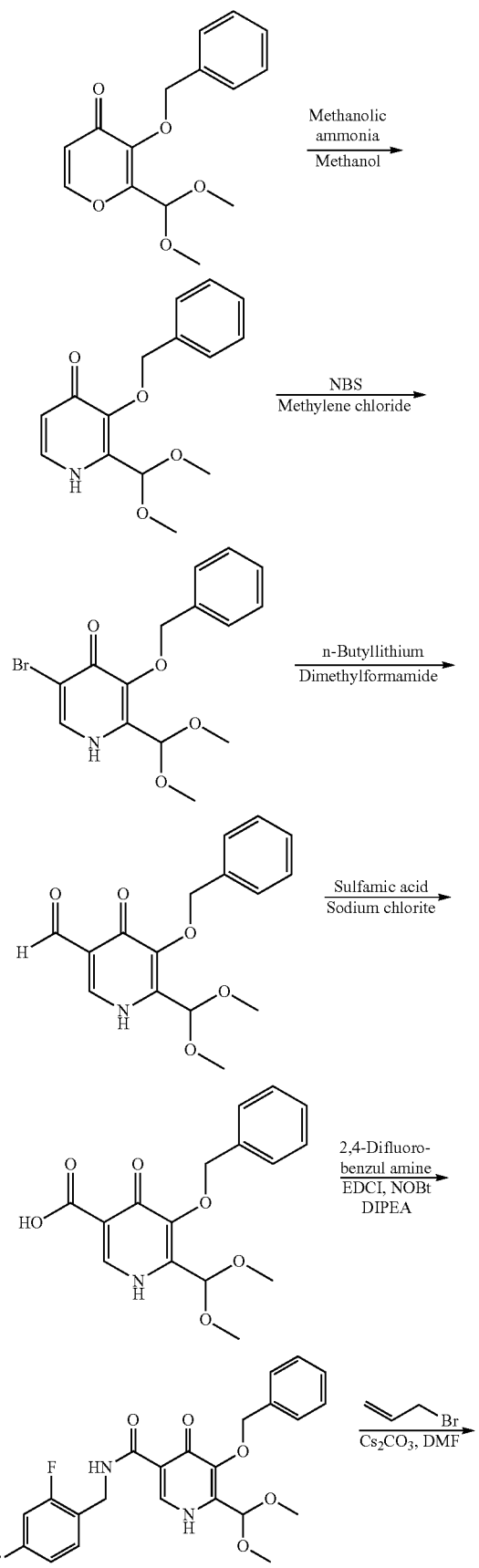

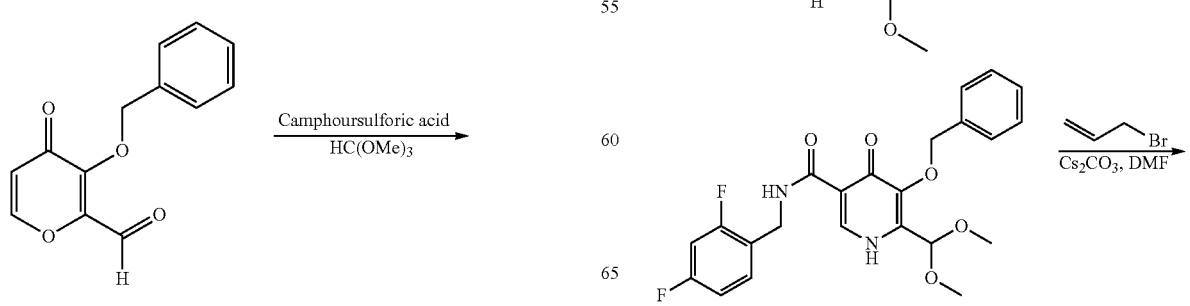

13
-continued
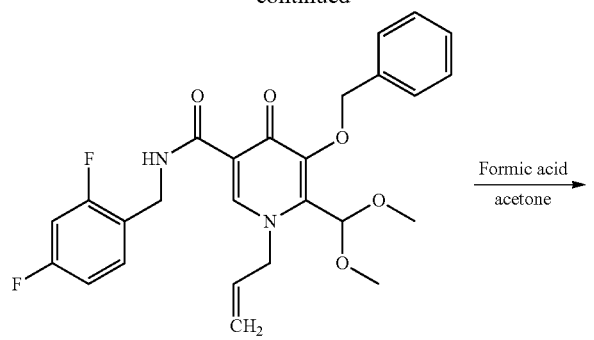
Formic acid
acetone
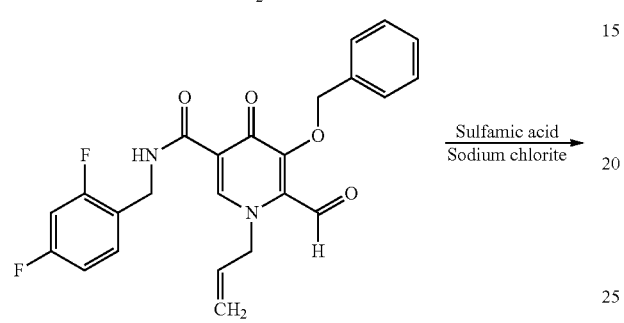
Sulfamic acid
Sodium chlorite
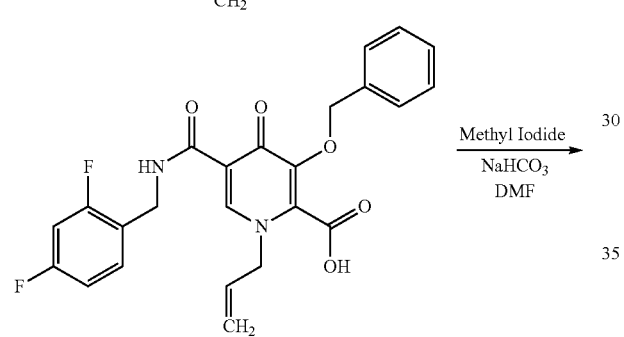
Methyl Iodide
NaHCO₃
DMF
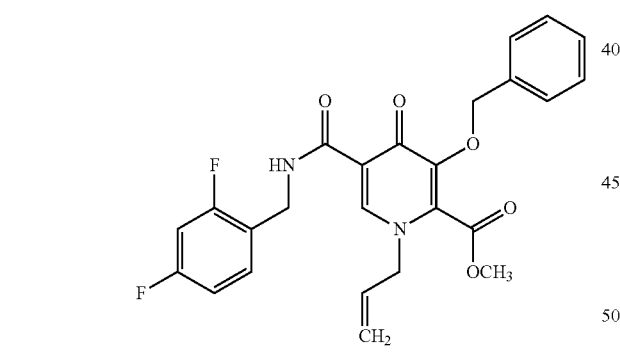
Method 2:
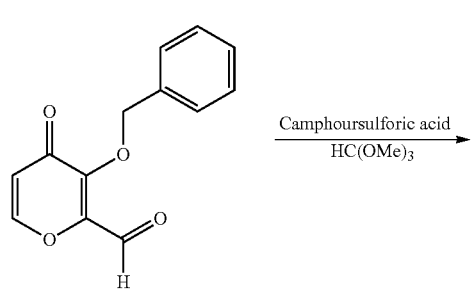
Camphoursulforic acid
HC(OMe)₃
14
-continued
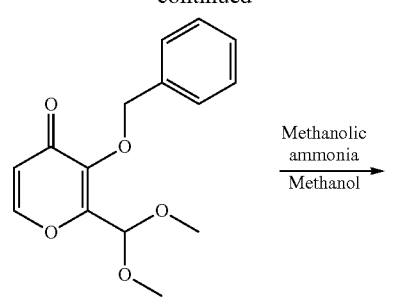
Methanolic
ammonia
Methanol
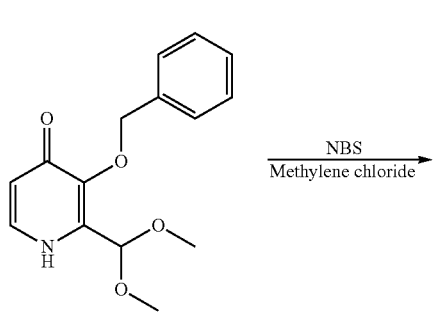
NBS
Methylene chloride
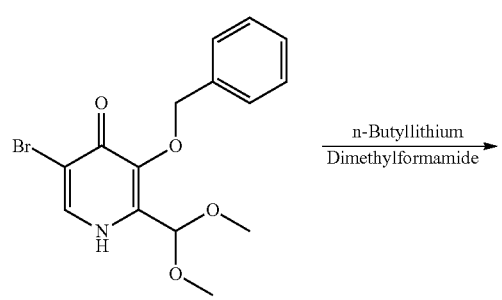
n-Butyllithium
Dimethylformamide
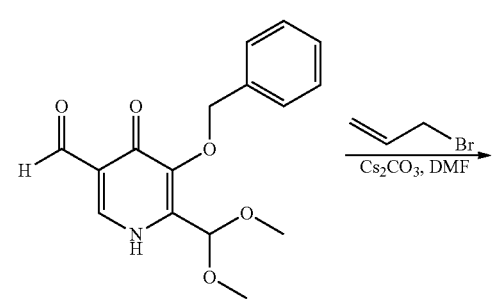
$\underset{Cs_2CO_3, DMF}{\overset{\diagup\!\!\diagdown\!\!Br}{\longrightarrow}}$
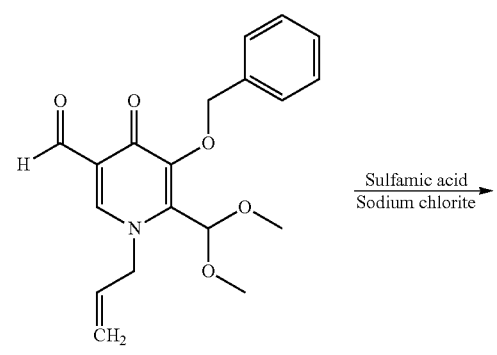
Sulfamic acid
Sodium chlorite

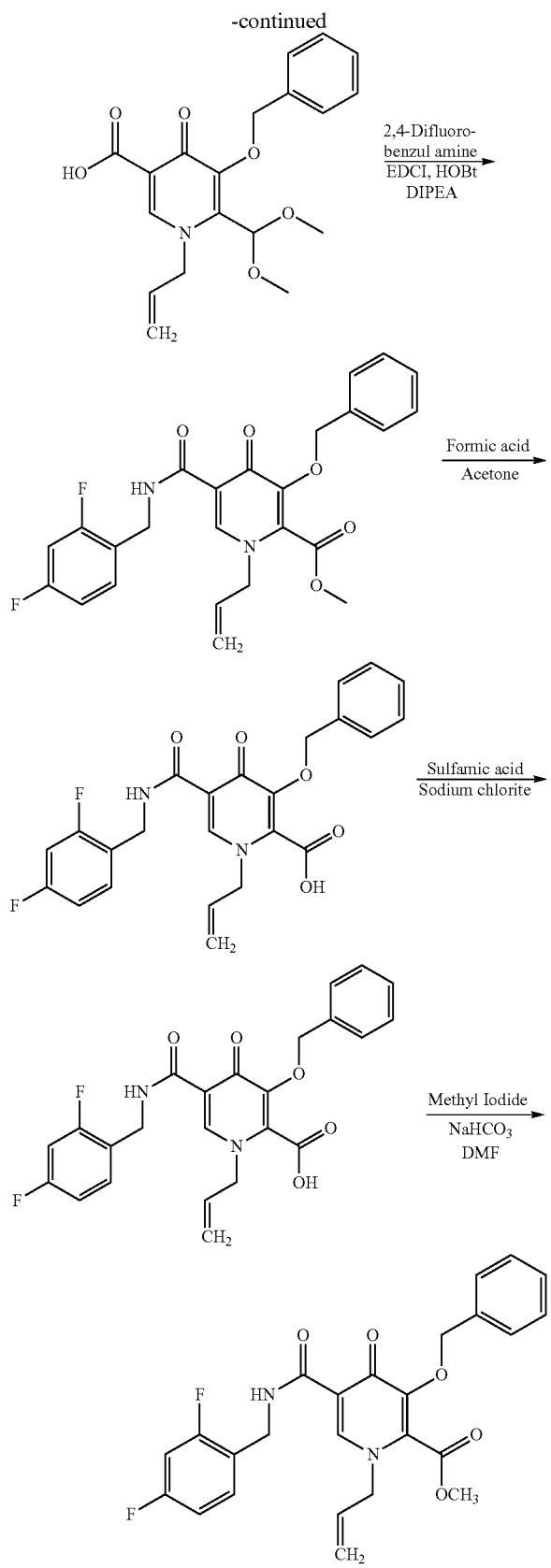

ment of human immunodeficiency virus (HIV)-1 infection. Hence it is advantageous to have alternate process for its preparation.

The main objective of the present invention is to provide an alternate process for the preparation of dolutegravir and pharmaceutically acceptable salts thereof.

BRIEF SUMMARY OF THE INVENTION

Accordingly, the present invention provides a novel process for the preparation of dolutegravir and pharmaceutically acceptable salts thereof.

In one aspect, the present invention provides a novel process for the preparation of dolutegravir of Formula I and pharmaceutically acceptable salts thereof,

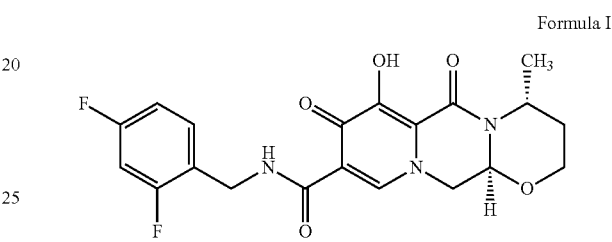
Formula I comprising:

a) reacting the compound of Formula II or a reactive derivative thereof

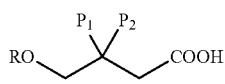
Formula II wherein "R" represents alkyl, aryl or aralkyl group and $P_1$ & $P_2$ independently represents a ketal protecting group or $P_1$ and $P_2$ together form a cyclic ring; with 2,4-difluoro benzylamine to provide a compound of Formula III, wherein R, $P_1$ & $P_2$ are defined as above;

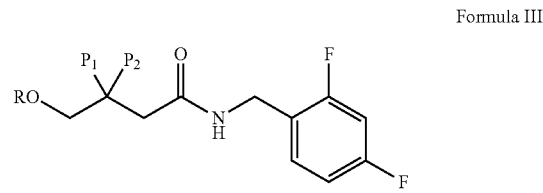
Formula III b) deprotecting the compound of Formula III to provide a compound of Formula IV; wherein R is defined as above;

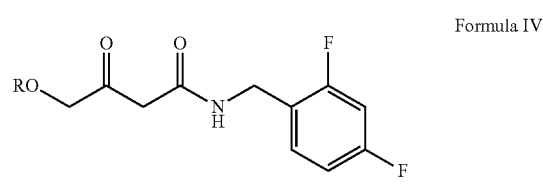
Formula IV c) converting the compound of Formula IV into a compound of Formula V; wherein R is defined as above;

Dolutegravir is one of the important drug which is recently approved and available in the market for the treat-

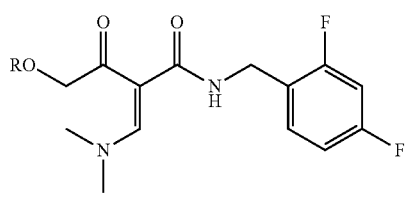
Formula V d) reacting the compound of Formula V with a compound of Formula VI, wherein $R_1$ & $R_2$ independently represents an alkyl;

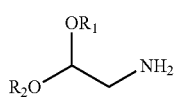
Formula VI to provide a compound of Formula VII; wherein R, $R_1$ & $R_2$ are defined as above;

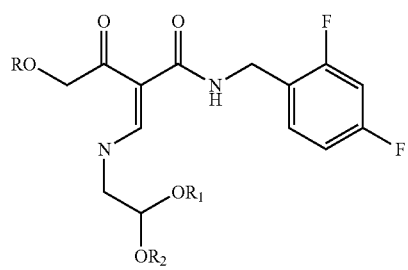
Formula VII e) condensing the compound of Formula VII with a compound of Formula VIII, wherein $R_3$ and $R_4$ is alkyl, aryl or aralkyl:

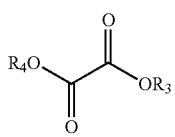
Formula VIII to provide a compound of Formula IX, wherein R, $R_1$, $R_2$ and $R_4$ are defined as above;

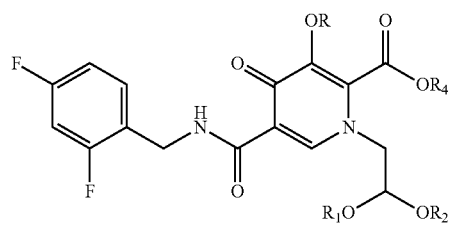
Formula IX f) converting the compound of Formula IX into a compound of Formula X, wherein R and $R_4$ are defined as above;

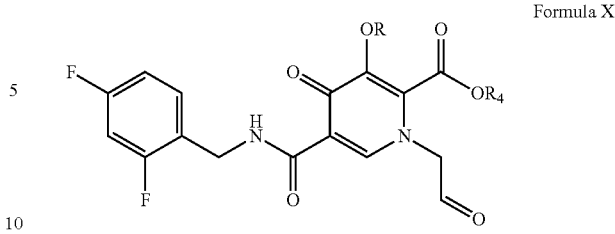
Formula X g) reacting the compound of Formula X with (R)-3-amino-1-butanol to provide a compound of Formula XI, wherein R is defined as above; and

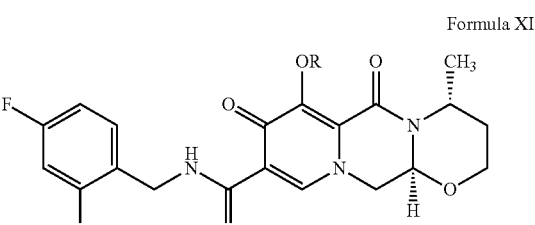
Formula XI h) converting the compound of Formula XI into dolutegravir of Formula I.

In another aspect, the present invention provides a novel process for the preparation of dolutegravir of Formula I and pharmaceutically acceptable salts thereof, comprising:

a) reacting the compound of Formula II or a reactive derivative thereof

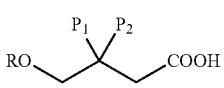
Formula II wherein "R" represents alkyl, aryl or aralkyl group and $P_1$ & $P_2$ independently represents a ketal protecting group or $P_1$ and $P_2$ together form a cyclic ring; with 2,4-difluoro benzylamine to provide a compound of Formula III, wherein R, $P_1$ & $P_2$ are defined as above;

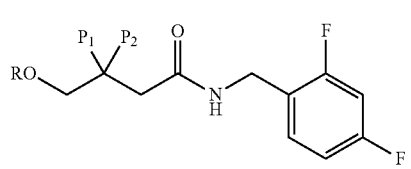
Formula III b) deprotecting the compound of Formula III to provide a compound of Formula IV; wherein R is defined as above;

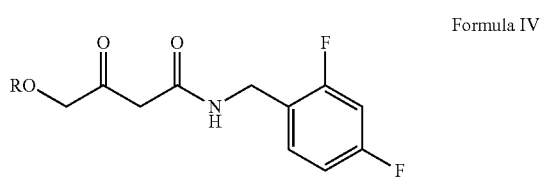
Formula IV c) converting the compound of Formula IV into a compound of Formula V; wherein R is defined as above;

Formula V

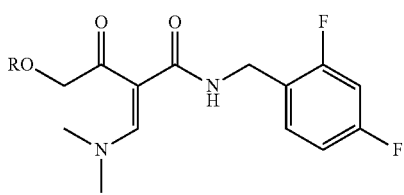

d) reacting the compound of Formula V with a compound of Formula VI, wherein $R_1$ & $R_2$ independently represents an alkyl;

Formula VI

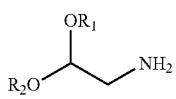

to provide a compound of Formula VII; wherein R, $R_1$ & $R_2$ are defined as above;

Formula VII

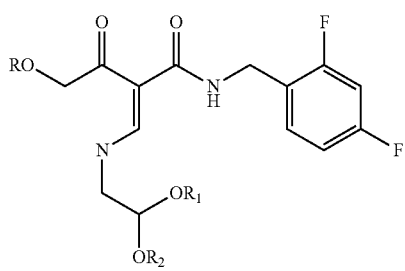

e) condensing the compound of Formula VII with a compound of Formula VIII, wherein $R_3$ and $R_4$ is alkyl, aryl or aralkyl;

Formula VIII

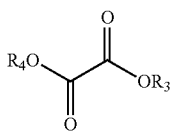

to provide a compound of Formula IX, wherein R, $R_1$, $R_2$ and $R_4$ are defined as above;

Formula IX

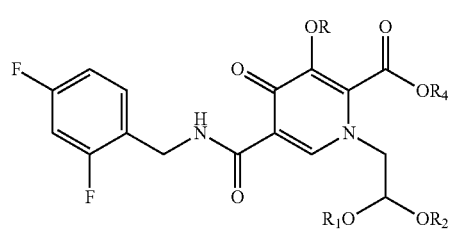

f) converting the compound of Formula IX into a compound of Formula X, wherein R and $R_4$ are defined as above;

Formula X

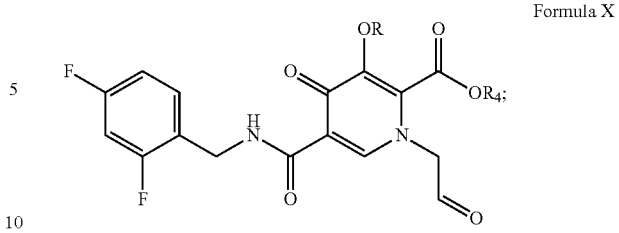

and g) converting the compound of Formula X into dolutegravir of Formula I.

In another aspect, the present invention provides a novel process for the preparation of dolutegravir of Formula I and pharmaceutically acceptable salts thereof, comprising:

a) reacting the compound of Formula II or a reactive derivative thereof

Formula II

wherein "R" represents alkyl, aryl or aralkyl group and $P_1$ & $P_2$ independently represents a ketal protecting group or $P_1$ and $P_2$ together form a cyclic ring; with 2,4-difluoro benzylamine to provide a compound of Formula III, wherein R, $P_1$ & $P_2$ are defined as above;

Formula III

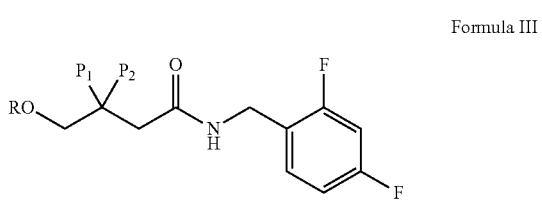

b) deprotecting the compound of Formula III to provide a compound of Formula IV; wherein R is defined as above;

Formula IV

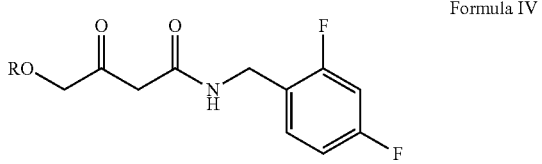

c) converting the compound of Formula IV into a compound of Formula V; wherein R is defined as above;

Formula V

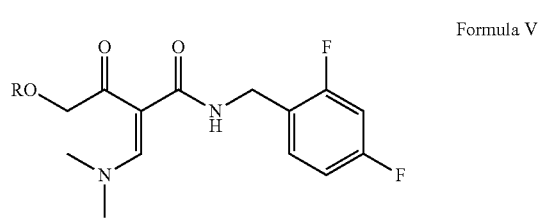

d) reacting the compound of Formula V with a compound of Formula VI, wherein $R_1$ & $R_2$ independently represents an alkyl;

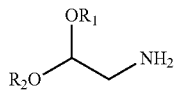

Formula VI to provide a compound of Formula VII; wherein R, $R_1$ & $R_2$ are defined as above;

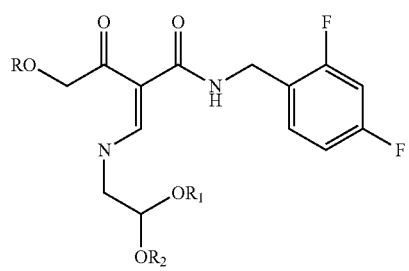

Formula VII e) condensing the compound of Formula VII with a compound of Formula VIII, wherein $R_3$ and $R_4$ is alkyl, aryl or aralkyl;

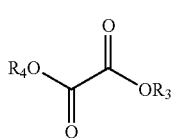

Formula VIII to provide a compound of Formula IX, wherein R, $R_1$, $R_2$ and $R_4$ are defined as above;

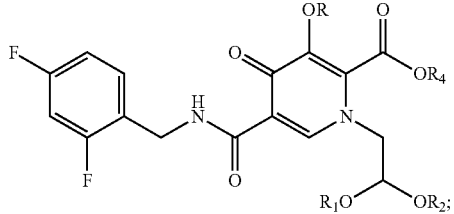

Formula IX and
f) converting the compound of Formula IX into dolutegravir of Formula I.

In another aspect, the present invention provides a novel process for the preparation of dolutegravir of Formula I and pharmaceutically acceptable salts thereof, comprising:

a) reacting the compound of Formula II or a reactive derivative thereof

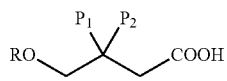

Formula II wherein "R" represents alkyl, aryl or aralkyl group and $P_1$ & $P_2$ independently represents a ketal protecting group or $P_1$ and $P_2$ together form a cyclic ring; with 2,4-difluoro benzylamine to provide a compound of Formula III, wherein R, $P_1$ & $P_2$ are defined as above;

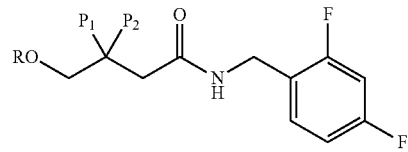

Formula III b) deprotecting the compound of Formula III to provide a compound of Formula IV; wherein R is defined as above;

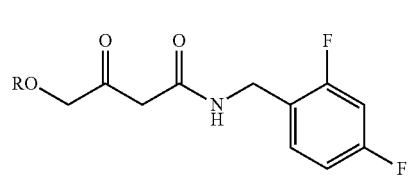

Formula IV c) converting the compound of Formula IV into a compound of Formula V; wherein R is defined as above;

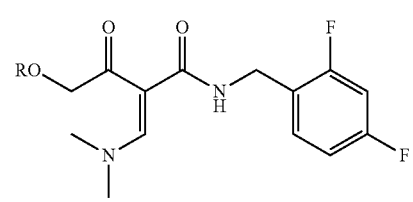

Formula V d) reacting the compound of Formula V with a compound of Formula VI, wherein $R_1$ & $R_2$ independently represents an alkyl;

Formula VI

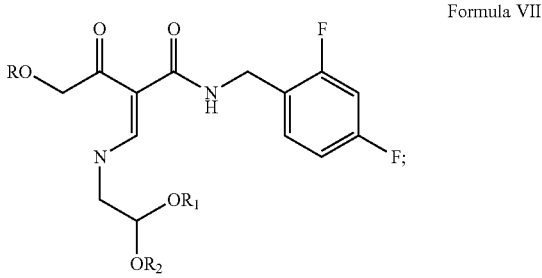

to provide a compound of Formula VII; wherein R, $R_1$ & $R_2$ are defined as above;

Formula VII and e) converting the compound of Formula VII into dolutegravir of Formula I.

In another aspect, the present invention provides a novel process for the preparation of dolutegravir of Formula I and pharmaceutically acceptable salts thereof, comprising:

a) reacting the compound of Formula II or a reactive derivative thereof

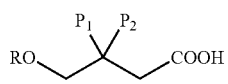

Formula II wherein "R" represents alkyl, aryl or aralkyl group and $P_1$ & $P_2$ independently represents a ketal protecting group or $P_1$ and $P_2$ together form a cyclic ring; with 2,4-difluoro benzylamine to provide a compound of Formula III, wherein R, $P_1$ & $P_2$ are defined as above;

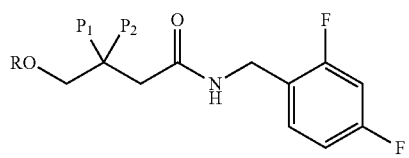

Formula III b) deprotecting the compound of Formula III to provide a compound of Formula IV; wherein R is defined as above;

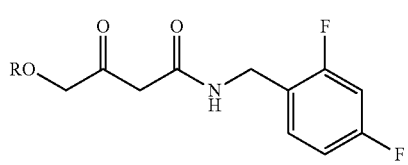

Formula IV c) converting the compound of Formula IV into a compound of Formula V; wherein R is defined as above;

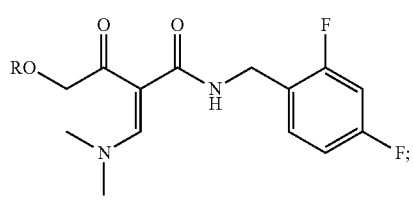

Formula V and d) converting the compound of Formula V into dolutegravir of Formula I.

In another aspect, the present invention provides a novel process for the preparation of dolutegravir of Formula I and pharmaceutically acceptable salts thereof, comprising:

a) reacting the compound of Formula II or a reactive derivative thereof

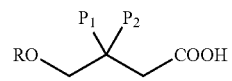

Formula II wherein "R" represents alkyl, aryl or aralkyl group and $P_1$ & $P_2$ independently represents a ketal protecting group or $P_1$ and $P_2$ together form a cyclic ring; with 2,4-difluoro benzylamine to provide a compound of Formula III, wherein R, $P_1$ & $P_2$ are defined as above;

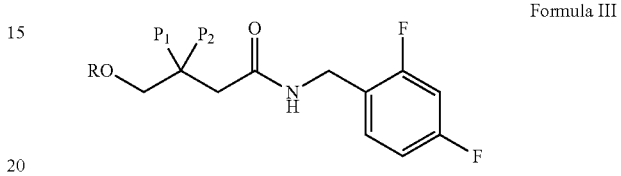

Formula III b) deprotecting the compound of Formula III to provide a compound of Formula IV; wherein R is defined as above;

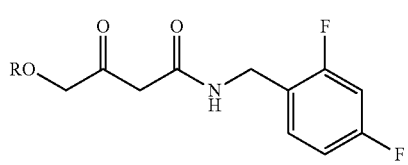

Formula IV and c) converting the compound of Formula IV into dolutegravir of Formula I.

In another aspect, the present invention provides a novel process for the preparation of dolutegravir of Formula I and pharmaceutically acceptable salts thereof, comprising:

a) reacting the compound of Formula II or a reactive derivative thereof

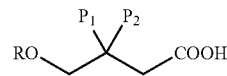

Formula II wherein "R" represents alkyl, aryl or aralkyl group and $P_1$ & $P_2$ independently represents a ketal protecting group or $P_1$ and $P_2$ together form a cyclic ring; with 2,4-difluoro benzylamine to provide a compound of Formula III, wherein R, $P_1$ & $P_2$ are defined as above;

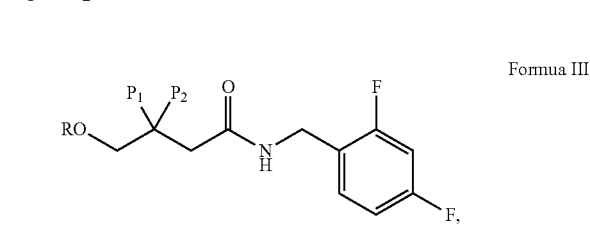

Formua III and b) converting the compound of Formula III into dolutegravir of Formula I.

In a further aspect, the present invention provides a process for the preparation of dolutegravir of Formula I and pharmaceutically acceptable salts thereof, comprising:

i) reacting the alkyl 4-haloacetoacetate of Formula XII, wherein X is halogen and $R_5$ is alkyl,

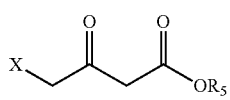

Formula XII with an alcohol of Formula ROH to provide the compound of Formula XIII

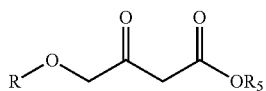

Formula XIII wherein R is alkyl, aryl or aralkyl; $R_5$ is defined as above;

ii) treating the compound of Formula XIII with ketal protecting agent to obtain compound of Formula XIV,

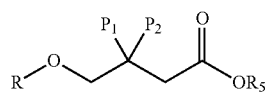

Formula XIV wherein $P_1$ & $P_2$ independently represents a ketal protecting group or $P_1$ and $P_2$ together form a cyclic ring and R & $R_5$ are defined as above, iii) hydrolyzing the compound of Formula XIV to obtain a compound of Formula II,

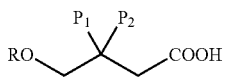

Formula II wherein $P_1$, $P_2$, & R are defined as above; and iv) converting the compound of Formula II into dolutegravir of Formula I.

In another aspect, the present invention provides a novel compound of Formula III

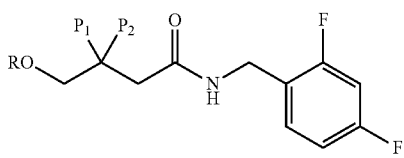

Formua III wherein "R" represents alkyl, aryl or aralkyl group and $P_1$ & $P_2$ independently represents a ketal protecting group or $P_1$ and $P_2$ together form a cyclic ring.

In another aspect, the present invention provides a novel compound of Formula IV

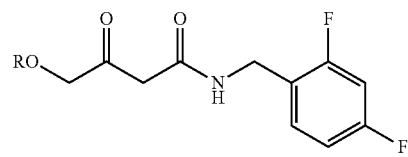

Formula IV wherein "R" represents alkyl, aryl or aralkyl group.

In another aspect, the present invention provides a novel compound of Formula V

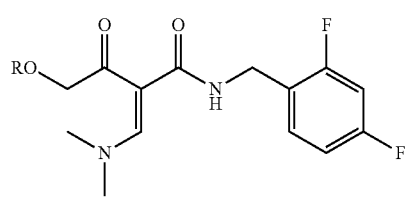

Formula V wherein "R" represents alkyl, aryl or aralkyl group.

In another aspect, the present invention provides a novel compound of Formula VII

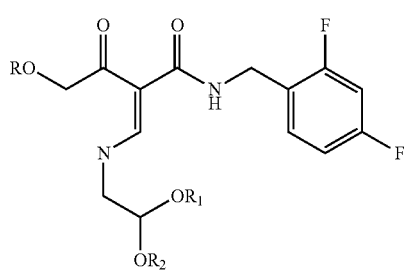

Formula VII wherein R represents alkyl, aryl or aralkyl group and $R_1$ & $R_2$ independently represents an alkyl group.

In another aspect, the present invention provides a novel compound of Formula IX

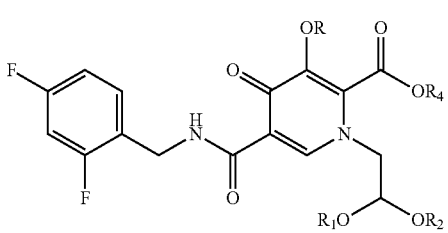

Formula IX wherein R & $R_4$ independently represents alkyl, aryl or aralkyl group and $R_1$ & $R_2$ independently represents an alkyl group.

In another aspect, the present invention provides a novel compound of Formula X

Formula X

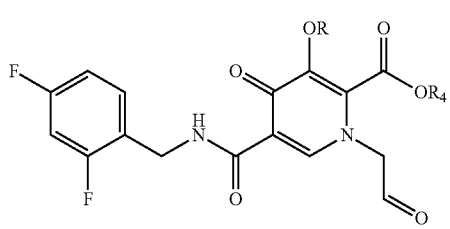

wherein R & R₄ independently represents alkyl, aryl or aralkyl group.

In another aspect, the present invention provides a novel compound of Formula XI Formula XI

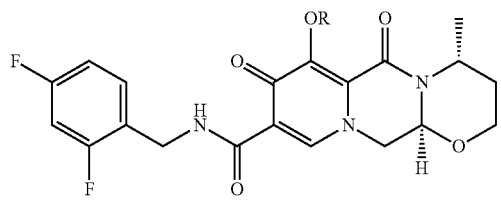

wherein R represents $C_{2-6}$ alkyl group.

In another aspect, the present invention provides a process for the preparation of dolutegravir of Formula I and pharmaceutically acceptable salts thereof, comprising:

a) reacting the compound of Formula IIB

Formula IIB

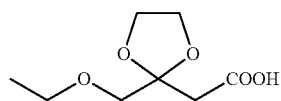

with 2,4-difluoro benzylamine to provide the compound of Formula IIIB,

Formula IIIB

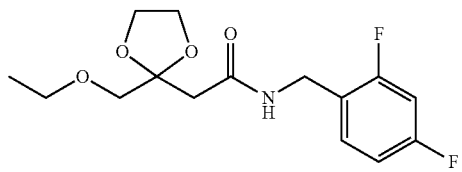

b) deprotecting the ketal protecting group of Formula IIIB to provide the compound of Formula IVB;

Formula IVB

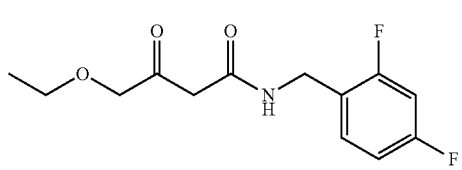

c) converting the compound of Formula IVB into the compound of Formula VB;

Formula VB

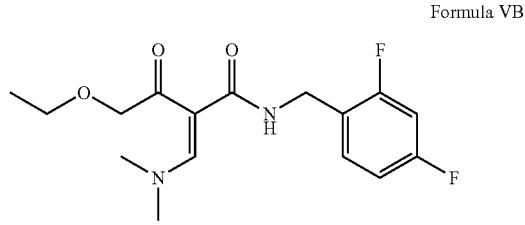 [SMILES: CCOCC(=O)/C(=C\N(C)C)C(=O)NCc1ccc(F)cc1F]

d) reacting the compound of Formula VB with the compound of Formula VIB

Formula VIB

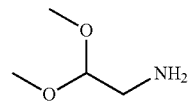

to provide the compound of Formula VIIB;

Formula VIIB

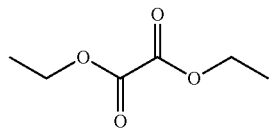

e) condensing the compound of Formula VIIB with the compound of Formula VIIIB

Formula VIIIB to provide the compound of Formula IXB,

Formula IXB

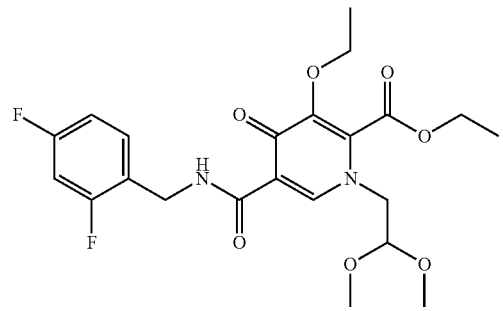

f) converting the compound of Formula IXB into the compound of Formula XB,

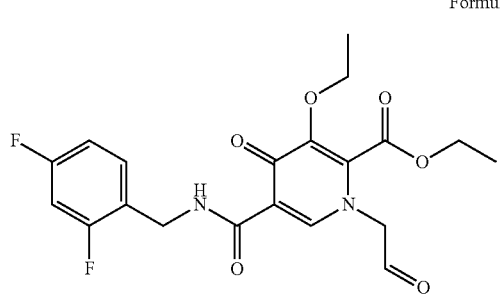

Formula XB g) reacting the compound of Formula XB with (R)-3-amino-1-butanol to provide the compound of Formula XIB, and

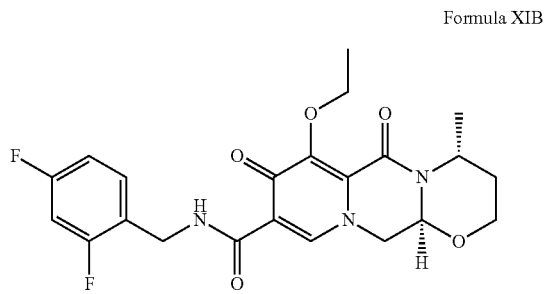 [SMILES: CCOc1c2n(cc(C(=O)NCc3ccc(F)cc3F)c1=O)C[C@@H]1OCC[C@@H](C)N1C2=O]

Formula XIB h) hydrolyzing the compound Formula XIB to provide dolutegravir of Formula I.

In another aspect, the present invention provides a pharmaceutical composition comprising dolutegravir and pharmaceutically acceptable salt thereof prepared by the process of the present invention and at least one pharmaceutically acceptable excipient.

DETAILED DESCRIPTION OF THE INVENTION

Unless otherwise specified the term "alkyl" used herein the specification represents $C_1$ to $C_6$ alkyl and is selected from but not limited to, methyl, ethyl, propyl, isopropyl, butyl, isobutyl, isoamyl and the like.

Unless otherwise specified the term "aryl" used herein the specification represents $C_{6-14}$ aryl and is selected from but not limited to, phenyl, napthyl and the like.

Unless otherwise specified the term "aralkyl" used herein the specification refers to an alkyl group substituted by an aryl group and may selected from but not limited to, benzyl, phenylethyl and the like.

Unless otherwise specified the term "ketal protecting group" used herein the specification represents dimethyl ketal, diethyl ketal, diisopropyl ketal, diisobutyl ketal, dibenzyl ketal and the like.

Unless otherwise specified the term "cyclic ring" used herein the specification represents the formation of cyclic ketals with alkylene glycols of the Formula HO(X)OH wherein X is alkyl, generally of 2 to 10 carbon atoms. For exemplary groups include, but are not limited to ethylene glycol, propylene glycol, butylene glycol, neopentyl glycol, 1,3-propane diol, 1,5-pentanediol, hexamethylene glycol and the like.

As used herein the specification, the term "nitriles" refers to acetonitrile, propionitrile, butyronitrile, isobutyronitrile, benzonitrile and the like; the term "ethers" refers to di-tert-butylether, diethylether, diisopropylether, di-n-butylether, 1,4-dioxane, methyltert-butyl ether, ethylisoproylether, ethyltert-butylether, tetrahydrofuran, 2-methyl tetrahydrofuran, anisole, dimethoxyethane and the like; the term "alcohols" refers to methanol, ethanol, n-propanol, isopropanol and n-butanol and the like; the term "chloro solvents" refers to methylene chloride, ethylene dichloride, carbon tetrachloride, chloroform and the like; the term "hydrocarbons" refers to benzene, chlorobenzene, toluene, xylene, heptane, hexane, cyclohexane, methyl cyclohexane, cyclopentane and the like; the term "ketones" refers to acetone, ethyl methyl ketone, diethyl ketone, methyl tert-butyl ketone, isopropyl ketone, isobutylmethyl ketone and the like; the term "esters" refers to ethyl acetate, methyl acetate, propylacetate, n-butyl acetate, isobutyl acetate, sec-butyl acetate, isopropyl acetate and the like; the term "amides" refers to dimethylacetamide, dimethylformamide, N-methylformamdide, dimethylimidazolidinone, N-methyl pyrrolidinone and the like; the term "sulfoxide solvents" refers to dimethylsulfoxide and the like.

The present invention provides a process for the preparation of dolutegravir and pharmaceutically acceptable salts thereof through novel intermediates.

Figure 1:
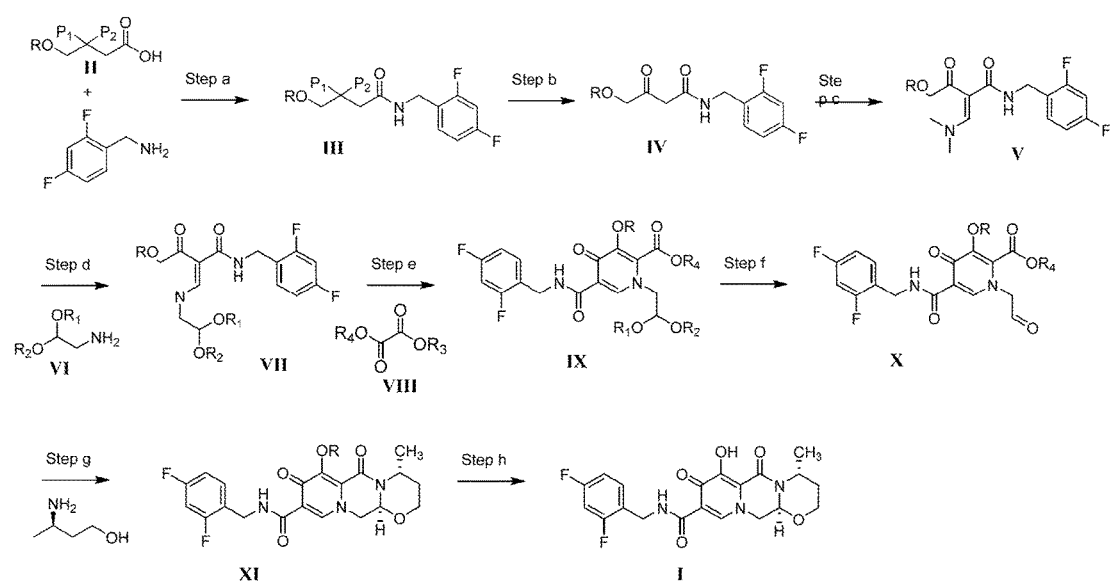
FIG. 1 is a general reaction sequence of the current invention.

In one embodiment, the present invention provides a novel process for the preparation of dolutegravir of Formula I and pharmaceutically acceptable salts thereof as shown in FIG. 1,

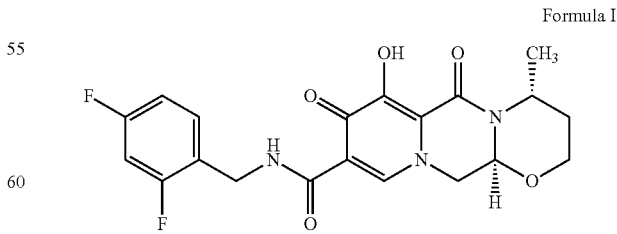

Formula I comprising:
a) reacting the compound of Formula II or a reactive derivative thereof with 2,4-difluoro benzylamine to provide a compound of Formula III,

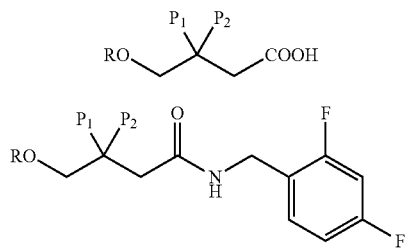

Formula II

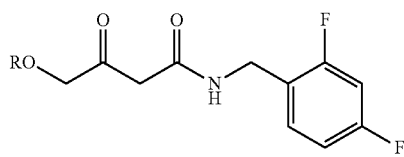

Formula III wherein R is alkyl, aryl or aralkyl group,
P₁ and P₂ independently represent a ketal protecting group, or together form a cyclic ring;

b) deprotecting the compound of Formula III to provide a compound of Formula IV;

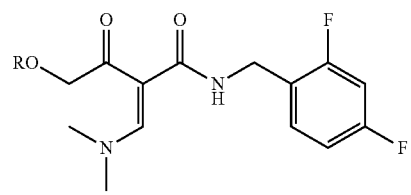

Formula IV c) converting the compound of Formula IV into a compound of Formula V;

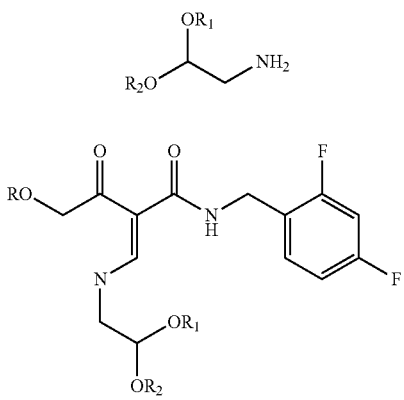

Formula V d) reacting the compound of Formula V with a compound of Formula VI to provide a compound of Formula VII, Formula VI Formula VII wherein R₁ and R₂ independently represent an alkyl;

e) condensing the compound of Formula VII with a compound of Formula VIII to provide a compound of Formula IX,

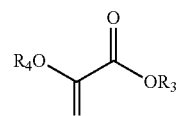

Formula VIII

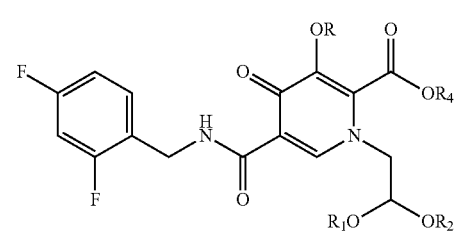

Formula IX wherein R₃ and R₄ are independently alkyl, aryl or aralkyl;

f) converting the compound of Formula IX into a compound of Formula X;

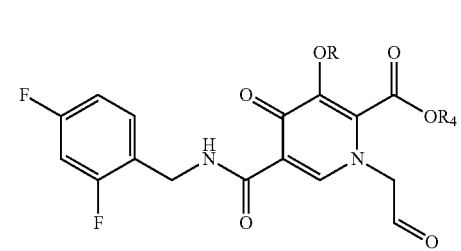

Formula X g) reacting the compound of Formula X with (R)-3-amino-1-butanol to provide a compound of Formula XI; and

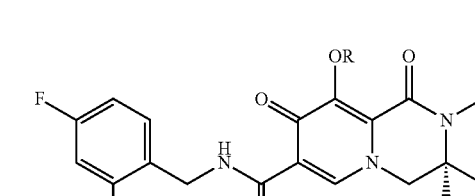

Formula XI h) converting the compound of Formula XI into dolutegravir of Formula I.

Step a)

Step a) of the foregoing process involves reacting the compound of Formula II, wherein "R" represents alkyl, aryl or aralkyl group and P₁ & P₂ independently represents a ketal protecting group or P₁ and P₂ together form a cyclic ring; with 2,4-difluoro benzylamine resulting the amide bond formation to provide the compound of Formula III.

Preferably the compound of Formula II can be a compound of Formula II, wherein "R" represents methyl, ethyl, isoamyl, or benzyl; and P₁ & P₂ together form a cyclic ring with ethylene glycol or propane diol.

The amide bond formation is occurred by general dehydration-condensation reaction, for example a method using a condensing agent, an acid chloride formation method or an acid anhydride formation method of the carboxyl group.

The amide bond formation may be carried out in the presence of a base and acid chloride forming agent such as chloroformates or coupling agent optionally in presence of additive in a suitable solvent. The reaction can be carried out at a suitable temperature.

The chloroformates for use herein include, but are not limited to ethyl chloroformate, isobutyl chloroformate, isopropenyl chloroformate and the like; preferably ethyl chloroformate.

The base used herein include, but are not limited to N-methyl morpholine (NMM), Di-isopropylethylamine (DIPEA) or Hunig base or triethylamine (TEA) and the like; preferably N-methyl morpholine.

Preferably the coupling agent used herein selected from the group comprising carbonyldiimidazole (CDI), carbonyldi(1,2,4-triazole),1-ethyl-3-(-3-dimethylamino propyl) carbodiimide (EDC), N,N'-Diisopropyl carbodiimide (DIC) and dicyclohexyl carbodiimide (DCC) and the like; and the additive used is selected from the group comprising hydroxy benzotriazole (HOBt), 1-hydroxy-7-azabenzotriazole (HOAt), 6-chloro-1-hydroxy-1H-benzotriazole (Cl-HOBt), hydroxypyridines (HOPy), imidazole or its salts, 1,8-diazabicyclo[5.4.0]undec-7-en (DBU), dimethyaminopyridine (DMAP), dimethyl amino pyridine pyridinium p-toluenesulfonate (DMAPPTS), tertiary amines, tertiary amine hydro halides and the like.

Preferably, the suitable solvents used herein are selected from the group consisting of nitriles, ethers, chloro solvents, hydrocarbons, esters, amides and mixtures thereof; preferably methylene chloride, tetrahydrofuran, ethylacetate, toluene or mixtures thereof.

It has been observed that when coupling reaction of 2,4-difluoro benzylamine with a compound of Formula II without ketal protections, an imine impurity of Formula A formed, which is difficult to remove at later stage of the synthesis. Thus, in order to control the imine impurity the process was optimized with protecting groups thereby enhancing the purity of the product.

Formula A

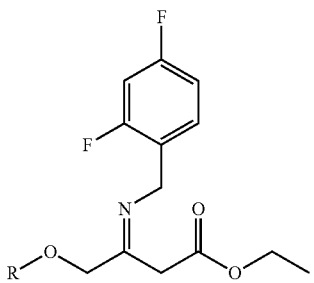

Step b)

Step b) of the foregoing process involves deprotection of protecting groups $P_1$ and $P_2$ of Formula III to obtain a compound of Formula IV. R represents alkyl, aryl or aralkyl group as described above, preferably methyl, ethyl, benzyl or isoamyl. $P_1$ and $P_2$ independently represent a ketal protecting group, or $P_1$ and $P_2$ together form a cyclic ring. Preferably $P_1$ and $P_2$ together form a 1,3-dioxalane ring with ethylene glycol or form a 1,3-dioxane with 1,3-propane diol. The deprotection reaction may be carried out with a suitable acid and a solvent and optionally in the presence of a phase transfer catalyst.

The suitable acid used herein is selected from the group consisting of hydrochloric acid, hydrobromic acid, acetic acid, sulfuric acid, p-toluene sulfonic acid, methane sulfonic acid and the like and mixtures thereof; preferably hydrochloric acid.

The solvent used herein for deprotection is selected from the group consisting of ethers, ketones, hydrocarbons, esters and mixtures thereof; preferably toluene, acetone, ethyl acetate and mixtures thereof; more preferably toluene.

Several classes of compounds are known to be capable of acting as phase transfer catalysts, for example quaternary ammonium compounds and phosphonium compounds, to mention just two. Phase transfer catalysts include, but are not limited to, at least one of tetramethyl ammoniumbromide, tetramethyl ammonium iodide, tetrabutyl ammoniumbromide, tetrabutyl ammoniumchloride, tetrabutylammonium iodide, tetrabutyl ammonium tribromide, tetrabutylammonium acetate, tetrabutyl ammonium fluoride, tetrabutylammonium hydroxide, tetrabutyl phosphonium bromide, tetramethyl ammonium chloride, tetraethylammonium chloride, methyl triethyl ammonium bromide, tetrabutylammonium hydrogensulfate, tricaprylyl methyl ammonium chloride, benzyl trimethylammonium bromide, benzyltriethylammonium bromide, benzyltrimethyl ammonium chloride, benzyltriethyl ammonium chloride, cetyltrimethyl ammonium bromide, cetylpyridinium bromide, N-benzylquininium chloride, benzyltributyl ammonium bromide, benzyltriethylammonium bromide, hexadecyltri ethyl ammonium chloride, hexadecyltrimethyl ammonium chloride, or octyltrimethylammonium chloride. The phase transfer catalysts are either-commercially available or readily synthesized by one of ordinary skill in the art. For example tricaprylylmethylammonium chloride, commonly known as Aliquat-336, is manufactured by Aldrich Chemical Company, Inc. Milwaukee, Wis.

Preferably, the phase transfer catalyst includes, but is not limited to, at least one of tetra butyl ammonium bromide, tetra butyl ammonium iodide, tetra butyl ammonium chloride, tetra butyl ammonium tribromide, tetra butyl phosphonium bromide, triethylbenzyl ammonium chloride, tetra methyl ammonium iodide, tetra butyl ammonium acetate, Aliquat-336 or tetra butyl ammonium fluoride.

The deprotection reaction may be carried out at a suitable temperature ranging from ambient to reflux temperature of the solvent used; preferably at about 65° C. to 100° C.

Step c)

Step c) of the foregoing process involves conversion of compound of Formula IV to Formula V by treating the compound of Formula IV with DMF-DMA (N,N-dimethyl-1,1-bis(methyloxy)methanamine) and optionally in presence of a solvent under conditions sufficient to form compound of Formula V.

Preferably the solvent used in step c) is selected from the group consisting of esters, ethers, chloro solvents, hydrocarbons, amides and mixtures thereof; preferably ethyl acetate, tetrahydrofuran, methylene chloride, toluene, dimethyl formamide and mixtures thereof; more preferably toluene, dimethyl formamide and mixtures thereof.

Step d)

Step d) of the foregoing process involves reaction of compound of Formula V with aminoacetaldehde dialkylacetal compound of Formula VI in a suitable solvent to obtain a compound of Formula VII. $R_1$ and $R_2$ independently represent an alkyl; preferably methyl. R is alkyl, aryl or aralkyl, preferably alkyl such as methyl, ethyl and isoamyl; aralkyl such as benzyl.

The suitable solvent used herein selected from the group consisting of alcohols, ethers, hydrocarbons, amides and mixtures thereof preferably methanol, tetrahydrofuran, toluene, dimethyl formamide and mixtures thereof more preferably toluene, dimethyl formamide and mixtures thereof.

Step e)

Step e) of the foregoing process involves condensation of Formula VII with a compound of Formula VIII to obtain a compound of Formula IX. R is alkyl, aryl or aralkyl, preferably alkyl such as methyl, ethyl and isoamyl; aralkyl such as benzyl. $R_1$ and $R_2$ independently represent alkyl, preferably methyl. $R_3$ and $R_4$ is alkyl, aryl or aralkyl, preferably methyl, or ethyl.

The step e) reaction is carried out in presence of a base and optionally a solvent. The base used herein for step e) include, but are not limited to alkali metal hydroxides such as lithium hydroxide, sodium hydroxide, potassium hydroxide, cesium hydroxide; alkali metal hydrides like sodium hydride, potassium hydride; alkali metal alkoxides such as sodium methoxide, sodium ethoxide, lithium methoxide, lithium ethoxide, sodium tert-butoxide, potassium tert-butoxide, sodium tert-pentoxide and the like; and mixtures thereof. Alternatively, an organic base may be used for example, an organic base such as a primary, secondary or tertiary amine. Representative examples of such amines include, but are not limited to, triethylamine, tributylamine, diisopropylethylamine, diethylamine, N-methylmorpholine, pyridine, 4-(N,N-dimethylamino)pyridine, N,N-dimethylaniline, N,N-diethylaniline and the like and mixtures thereof; preferably sodium methoxide, sodium ethoxide, sodium tert-butoxide, sodium tert-pentoxide and the like.

The solvent used herein for step e) is selected from the group consisting of hydrocarbons, esters and mixtures thereof; preferably toluene, xylene, ethyl acetate, methyl acetate, isopropyl acetate and the like; more preferably toluene. Further the condensation reaction may be carried out at a suitable temperature ranging from ambient to reflux temperature of the solvent used; preferably at about 50° C. to 85° C.

Step f)

Step f) of the foregoing process involves conversion of compound of Formula IX. R, $R_1$, $R_2$ and $R_4$ are described above.

The step f) reaction is advantageously carried out by treating the compound of Formula IX with a suitable acid at a suitable temperature for a suitable period effecting the conversion of Formula IX to Formula X.

Preferably the suitable acid used is selected from hydrochloric acid, hydrobromic acid, sulfuric acid, nitric acid, phosphoric acid, p-toluene sulfonic acid, methane sulfonic acid, formic acid, acetic acid, trifluoroacetic acid, maleic acid, oxalic acid and the like and mixtures thereof; preferably formic acid.

The step f) reaction may be carried out at a suitable temperature ranging from ambient to reflux temperature; preferably at about 65° C. to 85° C.

Step g)

Step g) of the foregoing process involves reaction of compound of Formula X with 3-amino-1-butanol in the presence of an acid and a solvent to obtain a compound of Formula XI. R is alkyl, aryl or aralkyl, preferably alkyl such as methyl, ethyl and isoamyl; aralkyl such as benzyl. $R_4$ is alkyl, aryl or aralkyl, preferably ethyl. 3-Amino-1-butanol preferably is an R-isomer.

The suitable acid used is selected from acetic acid, trifluoroacetic acid, formic acid and methanesulfonic acid and the like and mixtures thereof; preferably acetic acid.

The suitable solvent used for step g) is selected from the group consisting of nitriles, ethers, hydrocarbons, esters, amides and mixtures thereof; preferably methanol, toluene, ethyl acetate, dimethyl formamide; more preferably methanol, toluene and mixtures thereof.

Optionally the reaction of step g) may be carried out in the presence of alcohol solvent to improve the reaction rate. The suitable alcohol solvent used preferably is selected from methanol, ethanol, isopropanol and the like and mixtures thereof; more preferably methanol.

Step h)

Step h) of the foregoing process involves conversion of compound of Formula XI to dolutegravir by deprotection of compound of Formula XI with a suitable base in a suitable solvent.

The suitable base used herein for deprotection reaction is selected from alkali metal hydroxides such as lithium hydroxide, sodium hydroxide, potassium hydroxide, barium hydroxide, calcium hydroxide, cesium hydroxide; alkali metal hydrides such as sodium hydride, potassium hydride; alkali metal alkoxides such as sodium methoxide, sodium ethoxide, lithium methoxide, lithium ethoxide, sodium tert-butoxide, potassium tert-butoxide, sodium tert-pentoxide and the like; and mixtures thereof; preferably sodium hydroxide. The suitable solvent used herein selected from the group consisting of alcohols, ethers, sulfoxide, chloro solvents and mixtures thereof; preferably methanol, isopropanol, ethanol, methylene chloride, dimethyl sulfoxide and mixtures thereof.

The current invention also provides a novel compound of Formula III

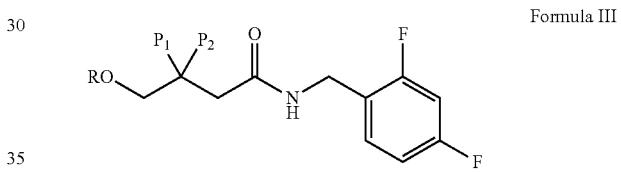

wherein "R" represents alkyl, aryl or aralkyl group and $P_1$ & $P_2$ independently represents a ketal protecting group or $P_1$ and $P_2$ together form a cyclic ring.

Examples of compounds of Formula III include the following:

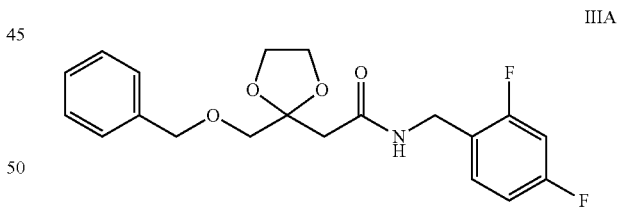

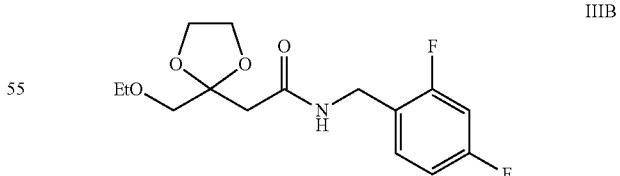

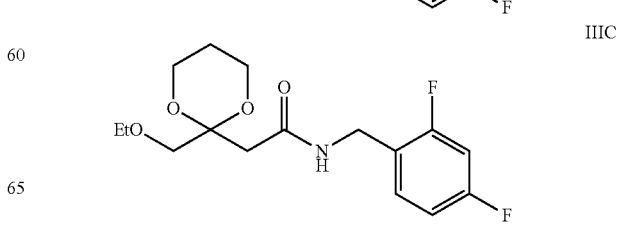

-continued

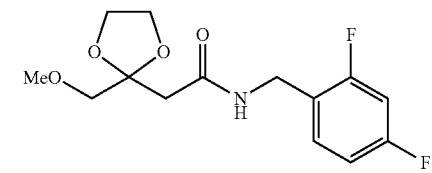
IIID

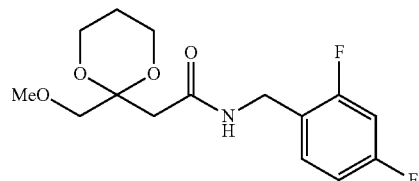
IIIE

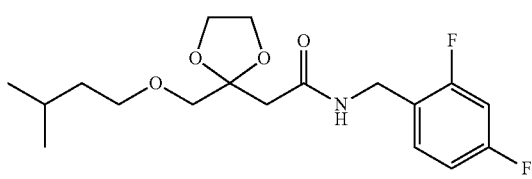
IIIF

In another embodiment, the present invention provides a novel compound of Formula IV

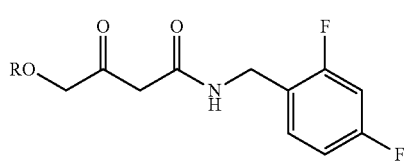
Formula IV wherein "R" represents an alkyl, aryl or aralkyl group.

In a preferred embodiment, the present invention provides novel compounds of Formulae IVA, IVB, IVC and IVD:

IVA

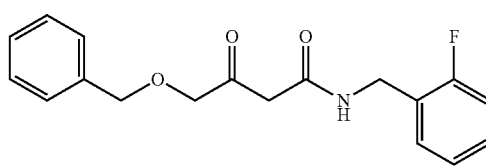

IVB

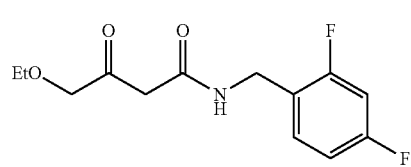

IVC

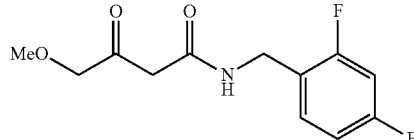

IVD

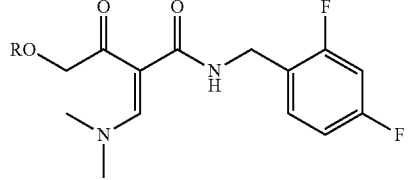

In another embodiment, the present invention provides a novel compound of Formula V

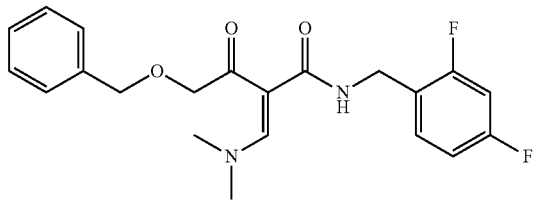
Formula V wherein "R" represents alkyl, aryl or aralkyl, preferably alkyl such as methyl, ethyl and isoamyl; aralkyl such as benzyl.

In a preferred embodiment, the present invention provides novel compounds of Formulae VA-VD:

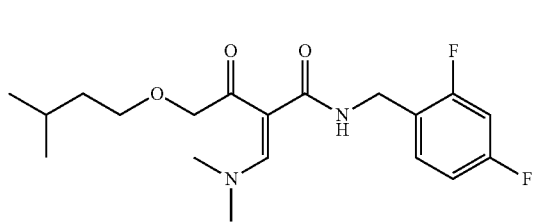

In another embodiment, the present invention provides a novel compound of Formula VII Formula VII

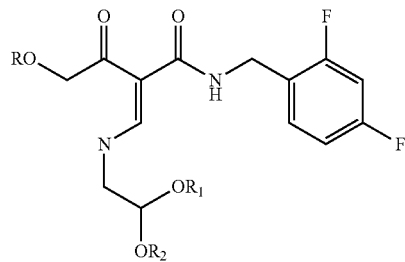

wherein "R" represents alkyl, aryl or aralkyl, preferably alkyl such as methyl, ethyl, and isoamyl; aralkyl such as benzyl; and $R_1$ & $R_2$ independently represent an alkyl, preferably methyl.

In a preferred embodiment, the present invention provides novel compounds of Formulae VIIA-VIID:

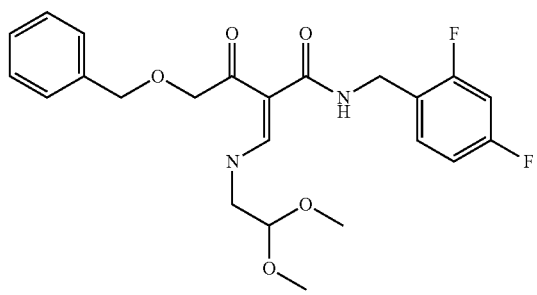
VIIA

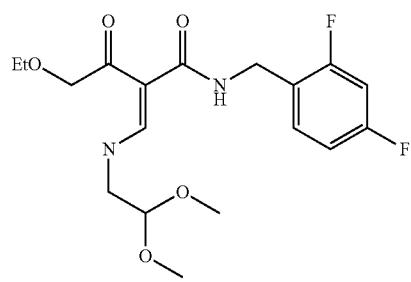
VIIB

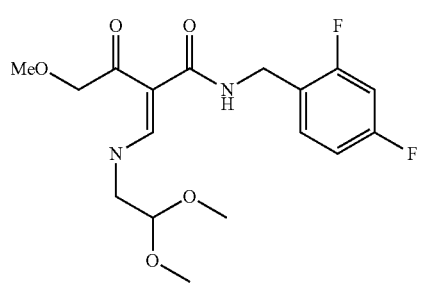
VIIC

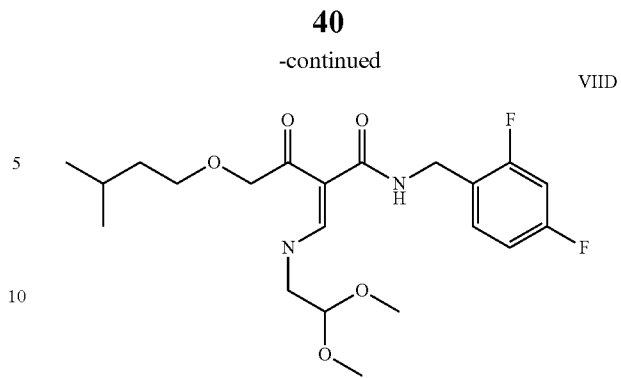
VIID

In another embodiment, the present invention provides a novel compound of Formula IX

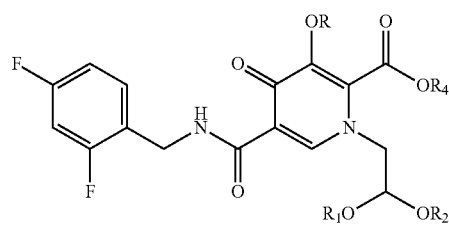
Formula IX wherein R is alkyl, aryl or aralkyl, preferably alkyl such as methyl, ethyl and isoamyl; aralkyl such as benzyl; $R_1$ and $R_2$ independently represent an alkyl, preferably methyl; and $R_4$ is alkyl, aryl or aralkyl, preferably ethyl; provided $R_4$ is not methyl when R is benzyl.

In another embodiment, the present invention provides novel compounds of Formulae IXA-IXD:

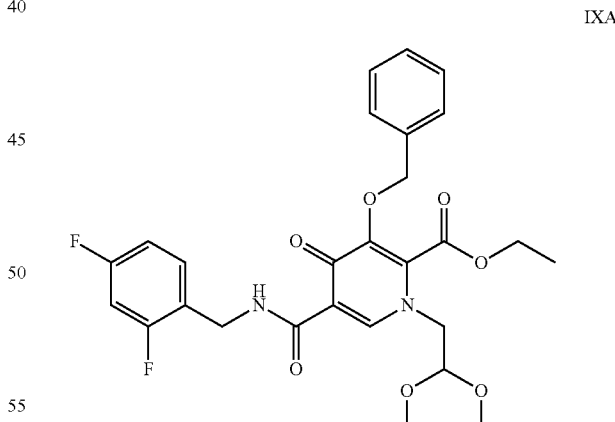
IXA

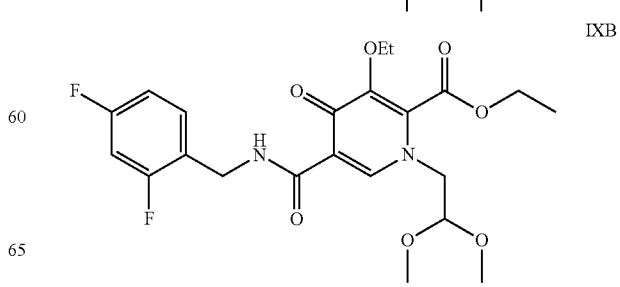
IXB

-continued

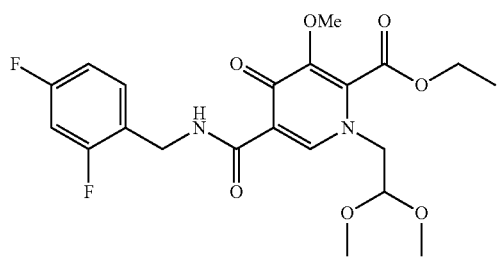
IXC

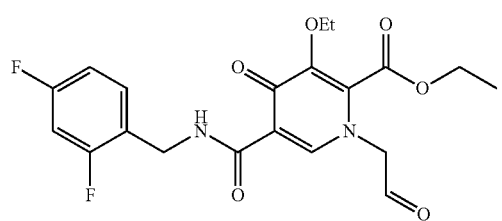
XB

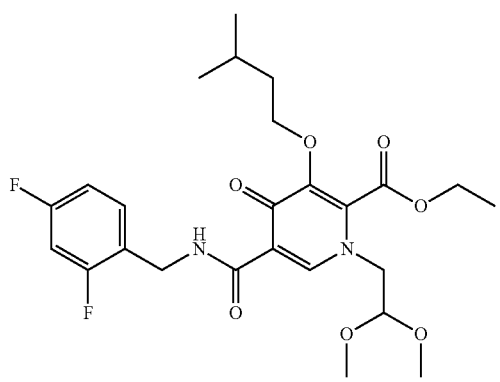
IXD

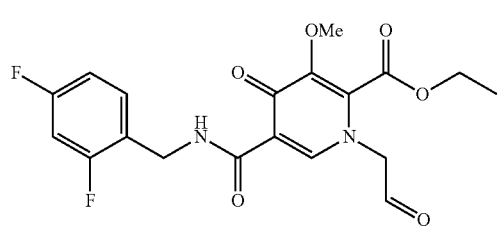
XC

XD

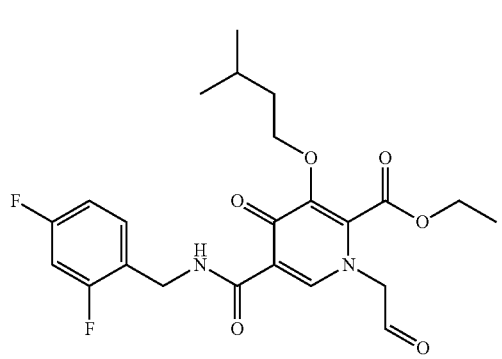

In another embodiment, the present invention provides a novel compound of Formula X

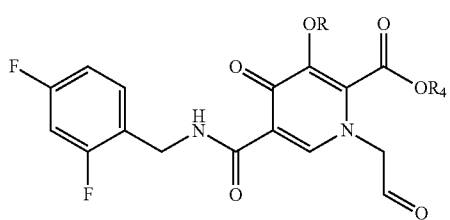
Formula X wherein R is alkyl, aryl or aralkyl, preferably alkyl such as methyl, ethyl and isoamyl; aralkyl such as benzyl; and $R_4$ is alkyl, aryl or aralkyl, preferably ethyl; provided $R_4$ is not methyl when R is benzyl.

In another embodiment, the present invention provides novel compounds of Formulae XA-XD:

XA

In another embodiment, the present invention provides a novel compound of Formula XI

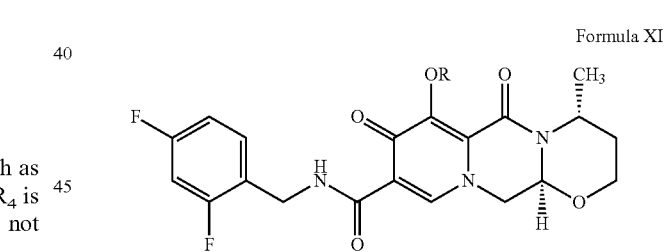
Formula XI wherein R is $C_{2-6}$ alkyl group.

In another embodiment, the present invention provides a novel compound of Formula XIB Formula XIB In a further aspect, the present invention provides a process for the preparation of dolutegravir of Formula I and pharmaceutically acceptable salts thereof, comprising:

i) reacting an alkyl 4-haloacetoacetate of Formula XII with an alcohol of ROH to provide a compound of Formula XIII, wherein X is halogen, $R_5$ is alkyl, and R is alkyl, aryl or aralkyl;

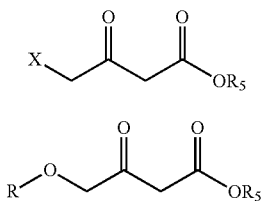

Formula XII

Formula XIII ii) treating the compound of Formula XIII with ketal protecting agent to obtain compound of Formula XIV, wherein $P_1$ and $P_2$ independently represent a ketal protecting group, or $P_1$ and $P_2$ together form a cyclic ring;

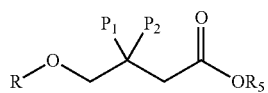

Formula XIV iii) hydrolyzing the compound of Formula XIV to obtain compound of Formula II; and

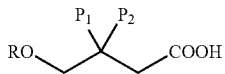

Formula II iv) converting the compound of Formula II into dolutegravir of Formula I.

In a preferred embodiment, the compound of Formula II may be prepared by a one-pot process without isolating the compounds of Formula XIII and Formula XIV of step i) and step ii).

Step i) of the foregoing process involves reaction of alkyl 4-haloacetoacetate of Formula XII with an alcohol ROH in the presence of a base and a solvent to provide the compound of formula XIII. X is halogen, preferably chloro. $R_5$ is alkyl, preferably ethyl. R is alkyl, aryl or aralkyl, preferably alkyl such as methyl, ethyl, isoamyl, and aralkyl such as benzyl.

Examples of a compound of Formula XIII include the following:

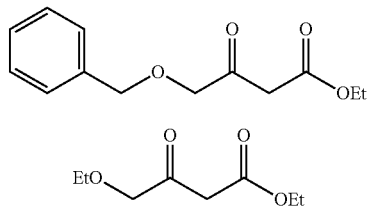

XIIIA

XIIIB

XIIIC

XIIID

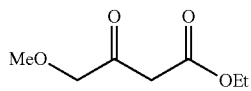

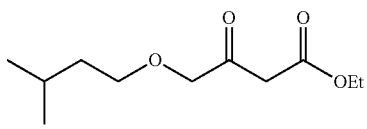

The suitable base used herein is selected from either inorganic or organic base, preferably inorganic bases like alkali metal hydroxides such as lithium hydroxide, sodium hydroxide, potassium hydroxide; alkali metal hydrides such as sodium hydride, potassium hydride; alkali metal alkoxides such as sodium methoxide, sodium ethoxide, lithium methoxide, lithium ethoxide, sodium tert-butoxide, potassium tert-butoxide, sodium tert-pentoxide, potassium tert-pentoxide and the like; and mixtures thereof; preferably sodium methoxide, sodium ethoxide, sodium tert-pentoxide or potassium tert-pentoxide.

The solvent used herein is selected from the group consisting of alcohols, ethers, esters, hydrocarbons, nitriles, ketones, amides, sulfoxide solvents and mixtures thereof; preferably methanol, ethanol, tetrahydrofuran, toluene and the like.

Step ii) of the foregoing process involves protection of compound of Formula XIII with a suitable protecting agent to provide the compound of formula XIV. R and $R_5$ are as described above. $P_1$ and $P_2$ independently represent a ketal protecting group, or $P_1$ and $P_2$ together form a cyclic ring. Preferably $P_1$ and $P_2$ together form a 1,3-dioxalane ring with ethylene glycol or form a 1,3-dioxane with 1,3-propane diol.

The suitable protecting agent used herein is selected from ketals such as dimethyl ketal, diethyl ketal, diisopropyl ketal, diisobutyl ketal, dibenzyl ketal and the like; or alkylene glycols of the Formula HO(X)OH wherein X is alkyl, generally of 2 to 10 carbon atoms. For exemplary groups include, but are not limited to ethylene glycol, propylene glycol, butylene glycol, neopentyl glycol, 1,3-propane diol, 1,5-pentanediol, hexamethylene glycol and the like; preferably ethylene glycol or 1,3-propane diol.

Further protection reaction of step ii) is suitably carried out in presence of a catalyst and optionally a solvent. Preferably the catalyst is acidic catalyst and examples of suitable acid catalysts are p-toluenesulfonic acid, sulfuric acid, acid ion exchangers, boron trifluoride complexes, ammonium chloride and the like; preferably p-toluenesulfonic acid. The solvent used herein may be selected from the group consisting of hydrocarbons, esters and mixtures thereof; preferably toluene.

Examples of a compound of Formula XIV include the following:

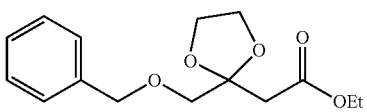

XIVA

XIVB

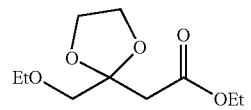

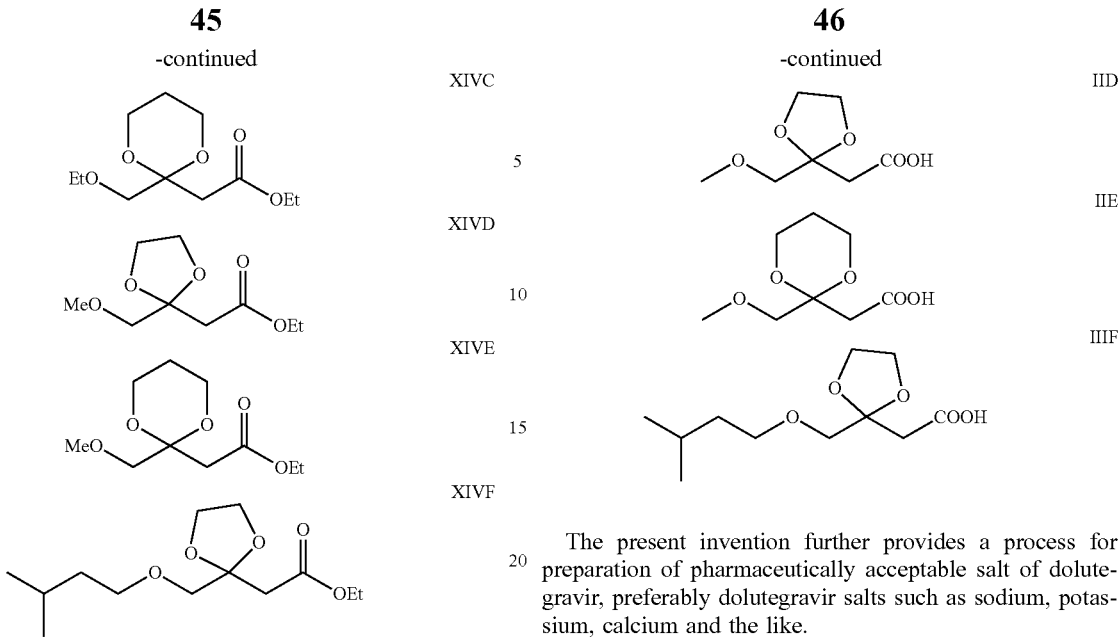

Step iii) of the foregoing process involves hydrolysis of compound of Formula XIV in the presence of a base and solvent, and optionally in presence of phase transfer catalyst to provide the compound of Formula II. R, $R_5$, $P_1$ and $P_2$ groups are as described above.

Preferably, the base used herein is selected from alkali metal hydroxides such as lithium hydroxide, sodium hydroxide, potassium hydroxide, barium hydroxide, calcium hydroxide, cesium hydroxide and the like and mixtures thereof; alkali metal alkoxides such as sodium methoxide, sodium ethoxide, lithium methoxide, lithium ethoxide, sodium tert-butoxide, potassium tert-butoxide, sodium tert-pentoxide and the like; and mixtures thereof; preferably sodium hydroxide, sodium ethoxide and the like.

The phase transfer catalyst used herein is selected from the group of catalysts defined as above.

Preferably, the solvent used herein for step iii) is selected from the group consisting of alcohols, ethers, ketones, hydrocarbons, nitriles, amides, chloro solvents, sulfoxide solvents, water and mixtures thereof; preferably tetrahydrofuran, toluene, water and mixtures thereof.

Examples of a compound of Formula II include the following:

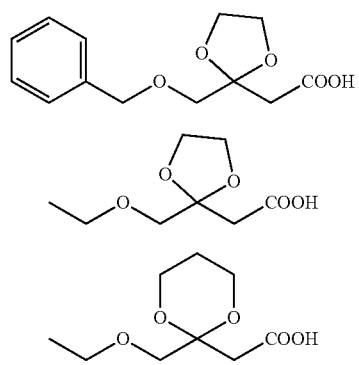

The present invention further provides a process for preparation of pharmaceutically acceptable salt of dolutegravir, preferably dolutegravir salts such as sodium, potassium, calcium and the like.

The present invention further provides a process for preparation of pharmaceutically acceptable salt of dolutegravir, for instance dolutegravir sodium, dolutegravir potassium or dolutegravir calcium, comprising:
a) providing a dolutegravir obtained by the processes described above in a suitable solvent to obtain a solution;
b) treating the solution with a corresponding cation source; and
c) isolating the dolutegravir salt.

The suitable solvent used herein for saltification is selected from the group consisting of hydrocarbon, chloro solvent, alcohols, ketones, nitriles, water and mixtures thereof; preferably ethanol, isopropanol, methylene chloride, water and the like and mixtures thereof.

The sodium source may be selected from the group consisting of sodium hydroxide, sodium methoxide, sodium ethoxide and the like. The potassium source includes KOH and other potassium salts. The calcium source includes calcium chloride, calcium acetate, calcium hydroxide and other calcium salts.

In one embodiment, the sodium salt of dolutegravir is prepared in 85% yield after treating dolutegravir with sodium hydroxide in a mixed ethanol and methylene chloride solvent, and subsequent workup in ethanol in the presence of sodium hydroxide.

In another embodiment, the present invention provides potassium salt of dolutegravir.

Figure 7:
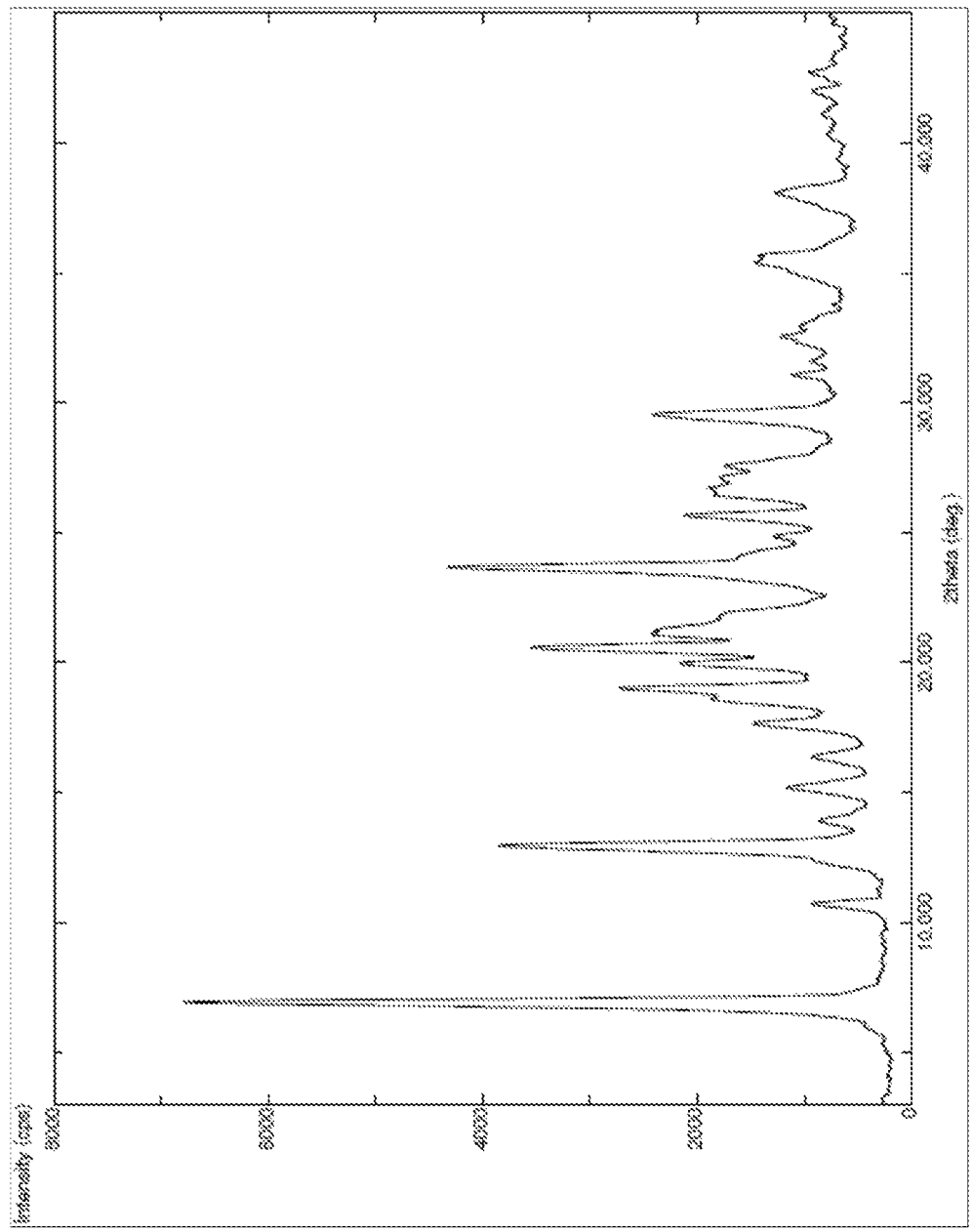
FIG. 7 is the PXRD spectrum of the potassium salt of dolutegravir prepared according to Example 52.

In another embodiment, the present invention provides potassium salt of dolutegravir characterized by a powder X-Ray diffraction (PXRD) pattern substantially in accordance with FIG. 7.

In another embodiment, the present invention provides potassium salt of dolutegravir characterized by a PXRD pattern having one or more peaks at about 6.94, 10.68, 12.32, 12.96, 15.20, 16.32, 17.66, 18.50, 19.00, 19.94, 20.58, 21.10, 21.74, 23.64, 24.08, 24.84, 25.62, 26.70, 27.14, 27.46, 29.54, 31.06, 32.52 and 35.38±0.2° 2θ.

In another embodiment, the present invention provides calcium salt of dolutegravir.

Figure 8:
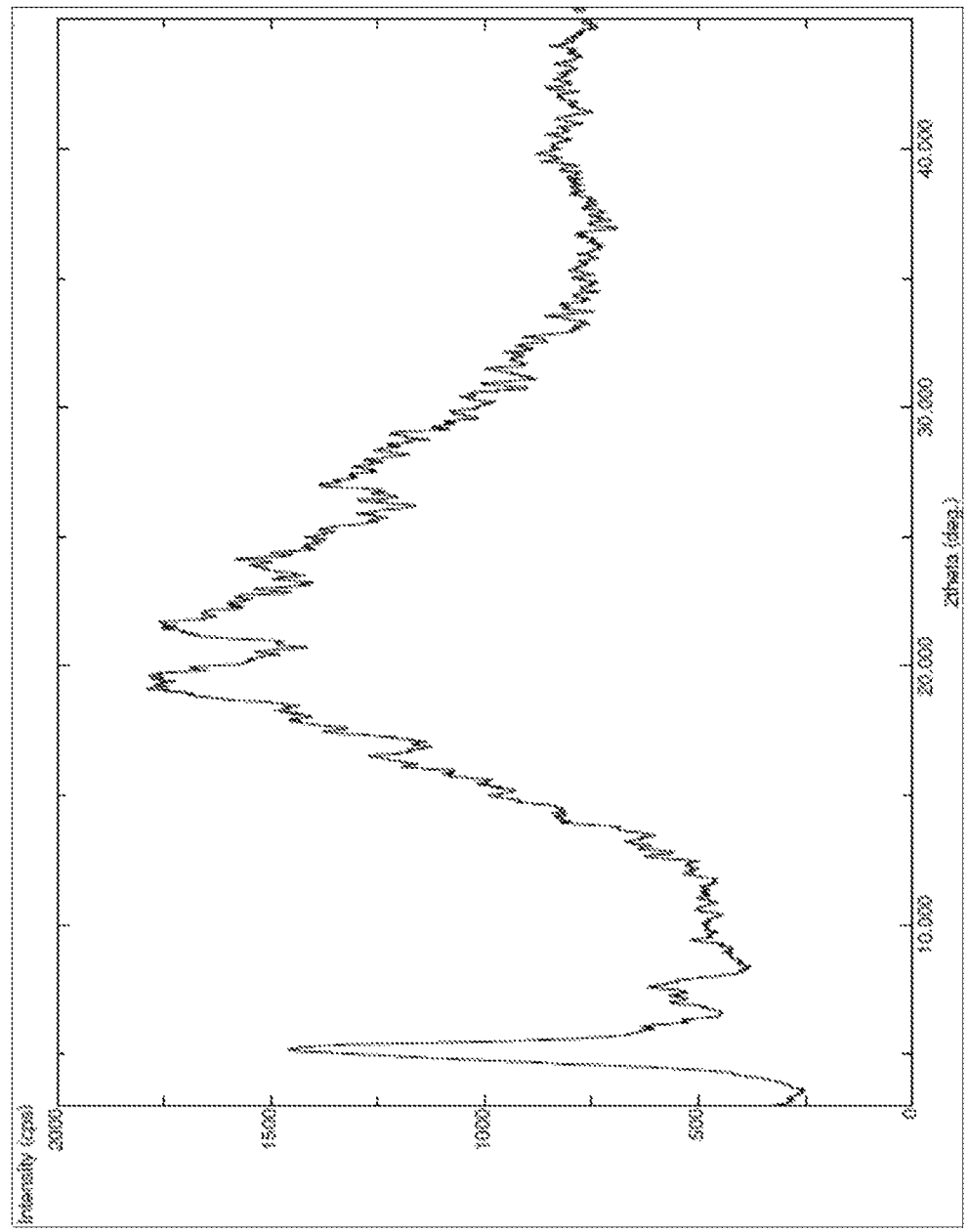
FIG. 8 is the PXRD spectrum of the calcium salt of dolutegravir prepared according to Example 53.

In another embodiment, the present invention provides calcium salt of dolutegravir characterized by a powder X-Ray diffraction (PXRD) pattern substantially in accordance with FIG. 8.

The present invention provides a dolutegravir and pharmaceutically acceptable salts thereof, obtained by the processes described herein, having a purity of at least about 97%, as measured by HPLC, preferably at least about 98% as measured by HPLC, and more preferably at least about 99.5%, as measured by HPLC.

In another embodiment, the present invention provides a pharmaceutical composition comprising the dolutegravir and pharmaceutically acceptable salts thereof prepared by the present invention, particularly dolutegravir sodium, potassium or calcium and at least one pharmaceutically acceptable excipient. Such pharmaceutical composition may be administered to a mammalian patient in any dosage form, e.g., liquid, powder, elixir, injectable solution, etc.

In the current invention, novel compounds of Formulae XIII, XIV, II, III, IV, V, VII, IX, X and XI are useful as intermediates in the preparation of dolutegravir and pharmaceutically acceptable salts thereof.

Figure 2:
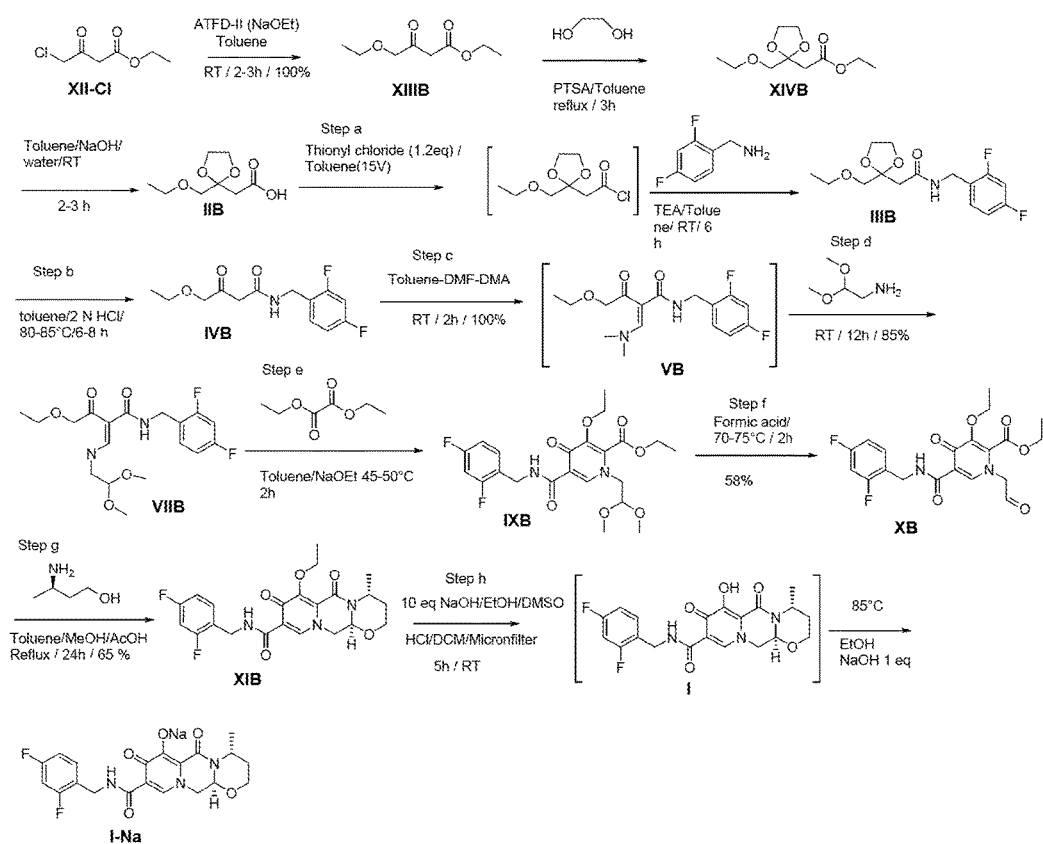
FIG. 2 is an example of synthesis of the sodium salt of dolutegravir.

In FIG. 2 is shown the reaction scheme employing intermediates of an ethyl ester and a 1,3-dioxane.

Figure 3:
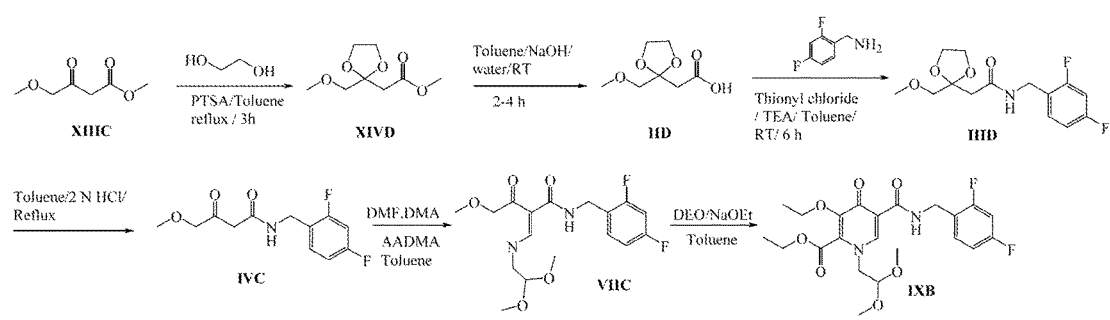
FIG. 3 is an example of synthesis of intermediates bearing a methyl ester and 1,3-dioxalane.

In FIG. 3 is shown the reaction scheme employing intermediates bearing a methyl ester and a 1,3-dioxalane. Upon treating VIIC with sodium ethoxide, the ethyl ester IXB is obtained from a methyl ester starting material VIIC.

Figure 4:
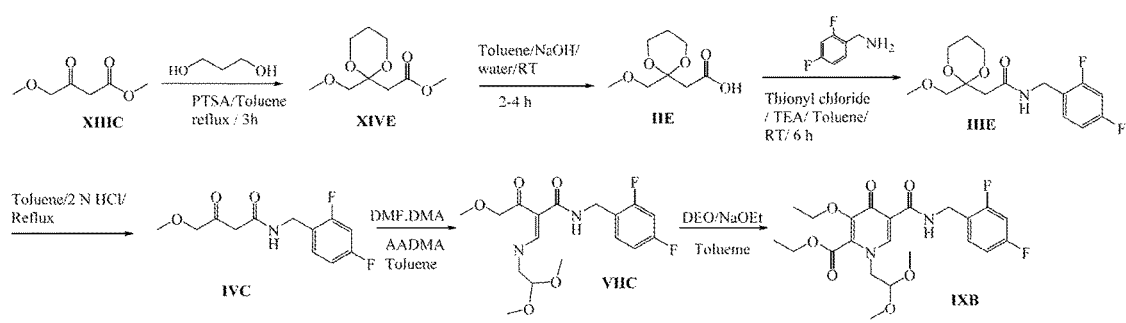
FIG. 4 is an example of synthesis of intermediates bearing a methyl ester and 1,3-dioxane.

In FIG. 4 is shown the reaction scheme employing intermediates bearing a methyl ester and a 1,3-dioxane. Just like in FIG. 3, the ethyl ester IXB is obtained from a methyl ester starting material VIIC upon treatment with sodium ethoxide.

Figure 5:
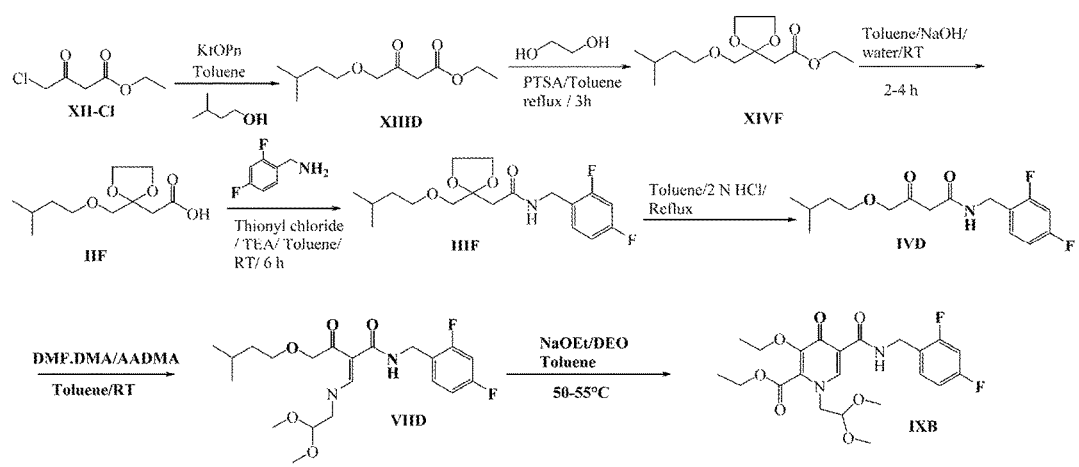
FIG. 5 is an example of synthesis of intermediates bearing a isoamyl ester and 1,3-dioxalane.

In FIG. 5 is shown the reaction scheme employing intermediates bearing an isoamyl ester and a 1,3-dioxane.

The current invention provides a method of preparing dolutegravir and pharmaceutically acceptable salts thereof that is cost effective and easily adaptable for large scale production. The current process avoids a large number of steps and tedious work-up procedures at all stages. A cheaper and safer solvent toluene is used generally throughout the synthetic sequence thus eliminates the expensive dichloromethane. The toluene used can be recovered and reused. Purification at all stages has been simplified and column chromatography used in the prior art is eliminated.

The step a) amide formation in the current process is via acid chloride, replacing the expensive and highly moisture sensitive coupling reagents such as CDI and HATU.

In the pyridione/pyrone ring formation step e) of the current process, the transformation employs the commercially available diethyl oxalate and sodium ethoxide in toluene at 45-50° C. Compared to one prior art method, the costly and non-commercially available sodium tert-pentoxide is avoided. Compared to another prior art method, the corrosive and difficult to handle ethyl oxalyl chloride is replaced with the commercially available diethyl oxalate, and the LiHMDS and the associated harsh temperature of −78° C. are replaced with sodium ethoxide and a milder 50-55° C. temperature. The yield of step e) is increased from the prior art 24% to around 75%.

In the current process, the expensive reagent R-3-aminobutanol is used at the very end of the synthetic sequence thus minimizing the cost. Also at the end of the reaction, no heavy metal such as Pd is needed for debenzylation thus eliminating the health risk by the presence of heavy metal in the final product. Because the current process does not involve bromine and carbon monoxide as in the prior art, the engineering cost is reduced.

In sum, the current process is efficient and cost effective and enables production on an industrial scale.

EXAMPLES

Example 1

Preparation of Compound of Formula XIIIA

Benzyl alcohol (95 mL, 1 eq) was added to a mixture of sodium tert-pentoxide (250 g, 2.5 eq) in tetrahydrofuran (750 mL, 5V) at 20-25° C. The reaction mass was heated to 40-45° C. and stirred for 2 hrs. The reaction mass was then cooled to 0-5° C. and ethyl-4-chloro acetoacetate (XII-Cl, 150 g, 1 eq) in tetrahydrofuran (750 mL, 5V) was added to it. The reaction mass was then stirred for 3 hrs at room temperature. After reaction completion, the reaction mass was cooled to 0-5° C. and pH was adjusted to ~2 using 20% hydrochloric acid. The reaction mass was extracted twice with ethyl acetate (2×5V). Organic layers were combined, washed with saturated bicarbonate solution (1×10V) followed by water (5V) and saturated brine solution (5V). Organic layer was dried over anhydrous sodium sulfate and distilled off the solvent completely to get the crude compound as brown oily thick liquid. The crude compound was purified by silica gel column chromatography (Eluent: EtOAc-hexane). The pure fractions were concentrated under vacuum to afford the title compound as pale yellow liquid (168 g, 78% yield). MS (ES): m/z 237 (M+H)$^+$.

Example 2

Preparation of Compound of Formula XIIIB

Ethanol (5.3 mL, 1.5 eq) was added to a mixture of sodium tert-pentoxide (16.7 g, 2.5 eq) and tetrahydrofuran (80 mL, 8V) at 20-25° C. The reaction mass was heated to 40-45° C. and stirred for an hour. The reaction mass was then cooled to 0-5° C. and ethyl 4-chloroacetoacetate (XII-Cl, 10 g, 1 eq) in tetrahydrofuran (20 mL, 2V) was added to it. The reaction mass was then stirred for an hour at 20-25° C. Upon completion, the reaction mass was cooled to 0-5° C. and pH of the reaction mass was adjusted to ~2 by using with 20% hydrochloric acid. The reaction mass was extracted twice with ethyl acetate (5V). The resulting organic layer was washed with saturated sodium bicarbonate solution (10V) followed by water (5V) and brine solution (5V). Organic layer was dried over anhydrous sodium sulfate and distilled off the solvent completely to get the title compound as brown oily liquid (9.1 g, 85.8% Yield). MS (ES): m/z 175 (M+H)$^+$.

In another experiment, to a solution of sodium ethoxide (3 eq) in toluene (4 vol) at 25° C. was added ethanol (1.5 eq). The resulting solution was cooled to 10-15° C., a solution of compound of Formula XII-Cl (1 eq) in Toluene (3 Vol) was added drop wise over a period of 20 min. The reaction mass was warmed to 40-45° C., progress of the reaction was monitored by TLC. After complete reaction, mass was cooled to 5-10° C., quenched with 2N HCl, organic layers were separated, aq phase further extracted with toluene, combined organic extracts were washed with saturated sodium bicarbonate solution. The organic layer was dried over Na$_2$SO$_4$, filtered and concentrated in vacuum to obtain compound of Formula XIIIB (85% yield). $^1$H NMR (300 MHz, CDCl$_3$): 4.2 (q, 2H), 4.11 (s, 2H), 3.56 (q, 2H), 3.53 (s, 2H), 1.21-1.27 (m, 6H). ESI-MS (m/z): 175 (M+1)$^+$.

Example 3

Preparation of Compound of Formula XIIID

To a solution of potassium tert pentoxide (3 eq) in Toluene (4 vol) at 25° C. was added isoamyl alcohol (2 eq). The resultant solution was cooled to 10-15° C., a solution of compound of Formula XII-Cl (1 eq) in Toluene (3 Vol) was added drop wise over a period of 20 min. Reaction mass was warmed to 40-45° C., progress of the reaction was monitored by TLC. Reaction mass was cooled to 5-10° C., quenched with 2N HCl, organic layers were separated, aq. layer further extracted with toluene, combined organic extracts were washed with saturated sodium bicarbonate solution. Organic layer was dried over $Na_2SO_4$, filtered and concentrated in vacuum to obtain crude compound of Formula XIIID Crude compound was purified by silica gel column chromatography with a gradient of 2-5% EtOAc in Hexanes provided compound of Formula XIIID (70% yield). $^1$H NMR (300 MHz, $CDCl_3$): 4.21 (q, 2H), 4.01 (s, 2H), 3.52 (t, 2H), 3.50 (s, 2H), 1.72-1.79 (m, 2H), 1.48-1.51 (m, 2H), 1.28 (t, 3H), 0.92 (d, 6H). ESI-MS (m/z): 217 $(M+1)^+$.

Example 4

Preparation of Compound of Formula XIVA

Compound of Formula XIIIA (wherein R=benzyl & $R_5$=ethyl; 168 g, 1 eq), toluene (1680 mL, 10V), paratoluene sulfonic acid monohydrate (13.5 g, 0.1 eq,) and ethylene glycol (168 mL, 1V) was heated to 105-110° C. and refluxed for about 2 hrs and water was removed by azeotropic distillation. Upon completion, the reaction mass was cooled to room temperature and poured into ice cold water (5V). Toluene layer was separated and the aqueous layer was extracted with ethyl acetate (2×5V). The resulting organic layer was combined and was washed with water (5V) followed by brine (5V) solution. Organic layer was dried over anhydrous sodium sulfate and distilled off the solvent completely to get the title compound as pale yellow oily liquid (199 g, 99.5% Yield). MS (ES): m/z 281 $(M+H)^+$ and 297 $(M+H)^+$.

Example 5

Preparation of Compound of Formula XIVB

Paratoluene sulfonic acid (0.98 g, 0.1 eq) was added to the compound of Formula XIIIB (wherein R & $R_5$=ethyl; 9.1 g 1 eq) in toluene (91 mL, 10V). Ethylene glycol (9.1 mL, 1V) was added to the reaction mass and heated to 100-110° C. then stirred for 3 hrs. Upon completion, the reaction mass was cooled to room temperature and poured into ice cold water. The reaction mass was extracted with ethyl acetate (5×5V) and the combined organic layer was washed with saturated sodium bicarbonate solution (2V). Organic layer was dried over anhydrous sodium sulfate and distilled off the solvent completely to get the title compound as oily liquid (9.7 g, 85% Yield) MS (ES): m/z 219 $(M+H)^+$ and 257 $(M+Na)^+$.

Example 6

Preparation of Compound of Formula XIVC

To a stirred solution of compound of Formula XIIIB (1 eq) in toluene (10 vol) was added PTSA (0.1 eq) at RT. 1, 3-Propane diol (1 Vol) was added to reaction mass at RT. Reaction mass was stirred for 4 hr at 100-110° C. Progress of the reaction was monitored by TLC. After complete reaction, solvent was completely distilled under vacuum. The resultant residue was purified by silica gel chromatography with a gradient of 10-20% EtOAc/hexane provided compound 3 (50% yield). $^1$H NMR (300 MHz, $CDCl_3$): 4.12-4.20 (q, 2H), 3.93-4.07 (m, 4H), 3.65 (s, 2H), 3.56-3.63 (q, 2H), 2.99 (s, 2H), 1.88-1.92 (m, 1H), 1.59-1.64 (m, 1H), 1.20-1.29 (m, 6H). ESI-MS (m/z): 233 $(M+1)^+$.

Example 7

Preparation of Compound of Formula XIVD

To a stirred solution of compound of Formula XIIIC (1 eq) in Toluene (10 vol) was added PTSA (0.1 eq) at RT. Ethylene glycol (1 Vol) was added to reaction mass at RT. Reaction mass was stirred for 4 hr at 100-110° C. Progress of the reaction was monitored by TLC. After complete reaction, solvent was completely distilled under vacuum. The resultant residue was purified by silica gel chromatography with a gradient of 10-20% EtOAc/hexane provided compound 3 (50% yield). $^1$H NMR (300 MHz, $CDCl_3$): 12.2 (s, 1H), 3.88 (s, 4H), 3.40 (s, 3H), 3.42 (s, 3H), 2.77 (s, 2H). ESI-MS (m/z): 191 $(M+1)^+$.

Example 8

Preparation of Compound of Formula XIVE

To a stirred solution of compound of Formula XIIIC (1 eq) in Toluene (10 vol) was added PTSA (0.1 eq) at RT. 1,3-Propane diol (1 Vol) was added to reaction mass at RT. The reaction mass was stirred for 4 hr at 100-110° C. Progress of the reaction was monitored by TLC. After complete reaction, solvent was completely distilled under vacuum. The resultant residue was purified by silica gel chromatography with a gradient of 10-20% EtOAc/hexane provided compound of Formula XIVE (50% yield). $^1$H NMR (300 MHz, $CDCl_3$): 3.94-4.02 (m, 4H), 3.69 (s, 2H), 3.60 (s, 3H), 3.43 (s, 3H), 2.97 (s, 2H), 1.86-1.90 (m, 2H). ESI-MS (m/z): 227 $(M+1)^+$.

Example 9

Preparation of Compound of Formula XIVF

To a stirred solution of compound of Formula XIIID (1 eq) in Toluene (10 vol) was added PTSA (0.1 eq) at RT. Ethylene glycol (1 Vol) was added to reaction mass at RT. Reaction mass was stirred for 4 hr at 100-110° C. Progress of the reaction was monitored by TLC. After complete reaction, solvent was completely distilled under vacuum. The resultant residue was purified by silica gel chromatography with a gradient of 10-20% EtOAc/hexane provided compound of Formula XIVF (50% yield). $^1$H NMR (300 MHz, $CDCl_3$): 4.11-4.18 (q, 2H), 4.0-4.12 (m, 4H), 3.5-3.54 (m, 4H), 2.76 (s, 2H), 1.62-1.69 (m, 1H), 1.44-1.51 (m, 2H), 1.24-1.29 (t, 3H), 0.88-0.9 (d, 6H). ESI-MS (m/z): 261 $(M+1)^+$.

Example 10

Preparation of Compound of Formula IIA

Aqueous sodium hydroxide solution (85.7 g in 2 Lt of water) was added to compound of Formula XIVA (200 g) dissolved in tetrahydrofuran (2V) at room temperature. The reaction mass was stirred for 2 hrs at room temperature. Upon completion, the reaction mass was washed with ethyl acetate (5V). Aqueous layer pH was adjusted to 1.9 by using dilute hydrochloric acid at below 10° C. The resulting aqueous layer was extracted with ethyl acetate (2×5V). Organic layer was washed with water (2V) followed by brine solution. Organic layer was dried over anhydrous sodium sulfate and concentrated under reduced pressure to get the title compound as yellow colour liquid (156 g, 86.6% Yield). MS (ES): m/z 253 (M+H)⁺ and 275 (M+Na)⁺.

Example 11

Preparation of Compound of Formula IIB

Aqueous sodium hydroxide solution (5.3 g, 3 eq, in 97 mL of water) was added to the compound of Formula XIVB (9.7 g, 1 eq) was dissolved in tetrahydrofuran (20 mL, 2V). The reaction mass was stirred at room temperature for 3 hrs. Upon completion, the reaction mass was washed with ethyl acetate (5V). Aqueous layer pH was adjusted to ~2 using 20% hydrochloric acid and the reaction mass was extracted with ethyl acetate (5×5V). Organic layer was separated and washed with water followed by brine solution then dried over anhydrous sodium sulfate. The organic layer was finally distilled off to get the title compound as light pale yellow oily liquid (5.9 g, 70% Yield). MS (ES): m/z 191 (M+H)⁺ and 213 (M+Na)⁺.

Example 12

Preparation of Compound of Formula IIB

A mixture of sodium ethoxide (51.8 g, 2.5 eq), toluene (200 ml, 4V) and ethanol (27.2 mL, 1.5 eq) was heated to 40-45° C. and stirred for an hour. The reaction mass was cooled to 20-25° C. and a solution of ethyl 4-chloroacetoacetate (50 g, 1 eq) in toluene (4V) was added to it. The reaction mass was heated to 50-55° C. and stirred for an hour. Upon completion, the reaction mass was cooled to 0-5° C. and reaction mass pH was adjusted to 2 by using with 2N hydrochloric acid. The organic layer was separated and aqueous layer was extracted with toluene (5V). Organic layers were combined and was washed with saturated sodium bicarbonate solution (10V) followed by water (5V) and brine solution (5V) then dried over anhydrous sodium sulfate. Paratoluene sulfonic acid monohydrate (5.8 g, 0.1 eq) and ethylene glycol (24.5 g, 1.3 eq) was added to the dried organic layer at 20-25° C. The reaction mass was heated to 100-110° C. and stirred for 5 hrs. Upon completion, the reaction mass was distilled off up to 5-6 volume and then allowed to cool to 20-25° C. Sodium hydroxide (48.7 g), water (250 mL, 5V) and tetra-n-butylammonium bromide (0.98 g, 0.01 eq) was added to the reaction mass and stirred for 4 hrs at 20-25° C. After reaction completion, the aqueous layer was separated and was washed with 10% methanol-methylene chloride (2×5V) mixture to remove nonpolar impurities. Aqueous layer was separated and pH was adjusted to 2 using aqueous hydrochloric acid at below 15° C. The aqueous layer was extracted with 10% methanol-methylene chloride (5×5V) and distilled off the solvent completely followed by co-distillation with toluene (2×1V) to get the title compound (40.5 g, 70% Yield) MS (ES): m/z 175 (M+H)⁺.

Example 13

Preparation of Compound of Formula IIC

To a stirred solution of compound of Formula XIVC (1 eq) in Toluene (5 vol) was added TBAB (0.01 eq) and NaOH (3 eq) dissolved in water (5 Vol) at RT. Reaction was maintained at 30-35° C. for 4 h. Progress of the reaction was monitored by TLC. After complete reaction, toluene layer was separated; aq. layer was washed with 10% MeOH in DCM. pH of the aq. layer was adjusted to ~1 using 6N HCl and was extracted with 10% MeOH in DCM. The organic layer was dried over anhydrous $Na_2SO_4$, filtered and concentrated under vacuum to obtain compound of Formula IIC (68% yield). ¹H NMR (300 MHz, $CDCl_3$): 10.2 (s, 2H), 3.98-4.03 (m, 4H), 3.69 (s, 2H), 3.57-3.65 (q, 2H), 2.99 (s, 2H), 1.76-1.82 (m, 2H), 1.21-1.26 (t, 3H). ESI-MS (m/z): 205 (M+1)⁺.

Example 14

Preparation of Compound of Formula IID

To a stirred solution of compound of Formula XIVD (1 eq) in Toluene (5 vol) was added TBAB (0.01 eq) and NaOH (3 eq) dissolved in water (5 Vol) at RT. Reaction was maintained at 30-35° C. for 4 h. Progress of the reaction was monitored by TLC. After complete reaction, toluene layer was separated; aq. layer was washed with 10% MeOH in DCM. pH of the aq. layer was adjusted to ~1 using 6N HCl and was extracted with 10% MeOH in DCM. The organic layer was dried over anhydrous $Na_2SO_4$, filtered and concentrated under vacuum to obtain compound of Formula IID (60% yield). ¹H NMR (300 MHz, $CDCl_3$): 12.16 (s, 1H), 3.88 (s, 4H), 3.40 (s, 2H), 3.28 (s, 3H), 2.55 (s, 2H). ESI-MS (m/z): 177 (M+1)⁺.

Example 15

Preparation of Compound of Formula IIE

To a stirred solution of compound of Formula XIVE (1 eq) in Toluene (5 vol) was added TBAB (0.01 eq) and NaOH (3 eq) dissolved in water (5 Vol) at RT. Reaction was maintained at 30-35° C. for 4 h. Progress of the reaction was monitored by TLC. After complete reaction, toluene layer was separated; aq. layer was washed with 10% MeOH in DCM. pH of the aq. layer was adjusted to ~1 using 6N HCl and was extracted with 10% MeOH in DCM. Organic layer was dried over anhydrous $Na_2SO_4$, filtered and concentrated under vacuum to obtain compound of Formula IIE (50% yield). ¹H NMR (300 MHz, $CDCl_3$): 12.07 (s, 1H), 3.94-4.08 (m, 4H), 3.66 (s, 2H), 3.44 (s, 3H), 2.97 (s, 2H), 1.75-1.83 (m, 2H). ESI-MS (m/z): 189 (M−1)⁺.

Example 16

Preparation of Compound of Formula IIF

To a stirred solution of compound of Formula XIVF (1 eq) in Toluene (5 vol) were added TBAB (0.01 eq) and NaOH (3 eq) dissolved in water (5 Vol) at RT. Reaction was maintained at 30-35° C. for 4 h. Progress of the reaction was monitored by TLC. After complete reaction, toluene layer was separated; aq. layer was washed with 10% MeOH in DCM. pH of the aq. layer was adjusted to ~1 using 6N HCl and was extracted with 10% MeOH in DCM. Organic layer was dried over anhydrous $Na_2SO_4$, filtered and concentrated under vacuum to obtain compound of Formula IIF (68% yield). ¹H NMR (300 MHz, $CDCl_3$): 4.02-4.08 (m, 4H), 3.51-3.56 (m, 4H), 2.82 (s, 2H), 1.66-1.71 (m, 1H), 1.44-1.51 (m, 2H), 0.882-0.90 (d, 6H). ESI-MS (m/z): 233 (M+1)⁺.

Example 17

Preparation of Compound of Formula IIIA

Ethyl chloroformate (65 mL, 1.1 eq) was added to a mixture of compound of Formula IIA (155 g, 1 eq) and N-methylmorpholine (82 mL, 1.2 eq) in THF (1.55 Lt., 10V) at 0-5° C. The reaction mass was stirred for 30 min at 10-15° C. The reaction mass was then cooled to 0-5° C. and 2,4-difluoro benzylamine (88 mL, 1.2 eq) in tetrahydrofuran (775 mL, 5V) was slowly added to it then stirred for an hour at room temperature. Upon completion, the reaction mass was quenched with water (1.55 Lt, 10V) and extracted with ethyl acetate (2×5V). Organic layer was separated and was washed with 10% aqueous hydrochloric acid (5V), water (5V) followed by sodium bicarbonate solution and brine solution (5V). Organic layer was dried over anhydrous sodium sulfate and distilled off under reduced pressure to get the title compound as crude (203 g). The obtained crude was purified from a mixture of 50% diisopropylether in heptane (5V) to get the pure title compound (185 g, 80% Yield). MS (ES): m/z 378 (M+H)$^+$.

Example 18

Preparation of Compound of Formula IIIB

Ethyl chloroformate (3.2 mL, 1.1 eq) was added to a mixture of compound of Formula IIB (5.9 g, 1 eq) and N-methylmorpholine (4.1 mL, 1.2 eq) in tetrahydrofuran (48 ml, 8V) at 0-5° C. The reaction mass was stirred for 30 min at 10-15° C. The reaction mass was then cooled to 0-5° C., 2,4-difluorobenzylamine (4.4 mL, 1.2 eq) in tetrahydrofuran (12 mL, 2V) was added to it and stirred for an hour at room temperature. After reaction completion, the reaction mass was poured in to ice cold water and extracted with ethyl acetate (2×5V). Organic layer was separated and was washed with 10% aqueous hydrochloric acid (5V), water followed by sodium bicarbonate (5V) and brine solution (5V). Organic layer was dried over anhydrous sodium sulfate and concentrated under reduced pressure. Thus obtained crude compound was purified by silica gel column (Eluent: EtOAc-hexane). Pure fractions were collected and distilled to get the title compound as pale yellow oily liquid (7 g, 71% Yield). MS (ES): m/z 316 (M+H)$^+$.

Example 19

Preparation of Compound of Formula IIIB

Ethyl chloroformate (90 mL, 1.2 eq) was added to a mixture of compound of Formula IIB (150 g) and N-methylmorpholine (112 mL, 1.3 eq) in tetrahydrofuran (8 v) at 0-5° C. The reaction was maintained for 30 min at 10-15° C. and then cooled to 0-5° C. 2,4-difluoro benzylamine (113 mL, 1.2 eq) in tetrahydrofuran (2V) was added to the reaction mass and stirred for an hour at room temperature. After reaction completion, the reaction mass was poured in to ice cold water (10V) and extracted with ethyl acetate (2×5V). Combined organic layer was washed with 10% aqueous hydrochloric acid (5V) followed by saturated sodium bicarbonate (5V), water (5V) and brine solution. Organic layer was dried over anhydrous sodium sulfate and the solvent was distilled off completely to get the title compound as light brown oil (234 g, 95%). MS (ES): m/z 316 (M+H)$^+$.

Example 20

Preparation of Compound of Formula IIIA

Compound of formula IIA (0.70 g) was dissolved in methylene chloride (10.5 mL). Diisopropyl carbodiimide (0.86 mL), dimethyl amino pyridine pyridinium p-toluenesulfonate (2.5 g) followed by 2,4-difluorobenzylamine (0.33 mL) was added to the reaction mass at room temperature and stirred for 3 hrs. After reaction completion, methylene chloride from the reaction mass was distilled off completely and the obtained solid was slurry washed with ethyl acetate. The solid was filtered off and the filtrate was washed with water. Organic layer was separated and dried over anhydrous sodium sulfate. Organic layer was distilled off completely to get the title compound (1 g).

Example 21

Preparation of Compound of Formula IIIB

A mixture of compound of formula IIB (1 g), dicyclohexylcarbodiimide (1.3 g), dimethylaminopyridine (100 mg) and tetrahydrofuran (10 mL) was stirred for 2 hrs at RT. The reaction mass was cooled to 0-5° C. and a solution of 2,4-difluorobenzylamine (0.76 ml) in tetrahydrofuran (5V) was added to it. The reaction mass was stirred for 12 hr at room temperature. After reaction completion, the reaction mass was filtered and the filtrate was concentrated under vacuum. The obtained crude was dissolved in methylene chloride and washed with aqueous hydrochloric acid, water followed by brine solution. Organic layer was dried over sodium sulfate and concentrated under reduced pressure to get brown oily liquid. The obtained crude was purified by silica-gel column (Eluent: 5-50% ethyl acetate in hexane) to get the pure title compound (0.98 g).

Example 22

Preparation of Compound of Formula IIIC

To a stirred solution of compound of Formula IIC (1 eq) in DCM (10 Vol) was added EDC.HCl (1.5 eq) and HOBT (1.5 eq) at RT. Reaction mass was stirred for 30 min. To the reaction mass a solution of 2,4-difluoro benzyl amine (1 eq) in DCM (5 Vol) was added at RT. Reaction was stirred at RT for 2 h. Progress of the reaction was monitored by TLC. After complete reaction, water was added to the reaction mass, layers separated and aq. layer was extracted with DCM. Combined all the organic layers and was washed with 2N HCl followed by saturated sodium bicarbonate solution. Organic layer was dried over anhydrous Na$_2$SO$_4$, filtered off and distilled to obtain compound of Formula IIIC (75% yield). $^1$H NMR (300 MHz, CDCl$_3$): 7.27-7.34 (m, 1H), 6.76-6.86 (m, 2H), 4.45 (d, 2H), 3.96 (t, 4H), 3.60 (s, 2H), 3.52 (q, 2H), 2.82 (s, 2H), 1.83 (—NH), 1.66-1.71 (m, 2H), 1.17 (t, 3H). ESI-MS (m/z): 330 (M+1)$^+$.

Example 23

Preparation of Compound of Formula IIID

To a stirred solution of compound of Formula IID (1 eq) in Toluene (5 Vol) and was cooled to 0-5° C. Thionyl chloride was added slowly at 0-5° C. over a period of 10 min. Reaction was stirred at RT for 30 min. Progress of the reaction was monitored by TLC, acid chloride was formed. In another RBF, 2, 4-difluoro benzyl amine (1 eq) in toluene (5 Vol) and trimethyl amine (3 eq) were taken at RT and was cooled to 5-10° C. Above formed acid chloride was added slowly to the RM at 5-10° C. Reaction mass was stirred at RT for 2 h. Progress of the reaction was monitored by TLC. After complete reaction, water was added to the reaction mass, layer separated and aq. layer was extracted with toluene. Combined all the organic layers and was washed with 2N HCl followed by saturated sodium bicarbonate solution. Organic layer dried over anhydrous Na$_2$SO$_4$, filtered off and distilled to obtain compound of Formula IIID (74% yield). $^1$H NMR (300 MHz, CDCl$_3$): 7.33-7.38 (m, 1H), 6.7-6.86 (m, 2H), 4.43 (d, 2H), 3.89-4.0 (m, 4H), 3.36 (s, 3H), 3.35 (s, 2H), 2.68 (s, 2H), 1.91 (s, —NH). ESI-MS (m/z): 302 (M+1)$^+$.

Example 24

Preparation of Compound of Formula IIIE

A stirred solution of compound of Formula ILE (1 eq) in Toluene (5 Vol) was cooled to 0-5° C. Thionyl chloride was added slowly at 0-5° C. over a period of 10 min. Reaction was stirred at RT for 30 min. Progress of the reaction was monitored by TLC, acid chloride was formed. In another RBF, 2,4-difluoro benzyl amine (1 eq) in toluene (5 Vol) and trimethyl amine (3 eq) were taken at RT. Reaction mass was cooled to 5-10° C. Above formed acid chloride was added slowly to the RM at 5-10° C. Reaction mass was stirred at RT for 2 h. Progress of the reaction was monitored by TLC. After complete reaction, water was added to the reaction mass, layers were separated and aq. layer was extracted with toluene. Combined all the organic layers and was washed with 2N HCl followed by saturated sodium bicarbonate solution. Organic layer dried over anhydrous $Na_2SO_4$, filtered off and distilled to obtain compound of Formula IIIE (60% yield). $^1$H NMR (300 MHz, $CDCl_3$): 7.36-7.39 (m, 1H), 6.77-6.86 (m, 2H), 4.65 (d, 2H), 4.32 (s, 3H), 3.98 (t, 4H), 3.57 (s, 2H), 2.88 (s, 2H), 1.75 (s, —NH), 1.63-1.70 (m, 2H). ESI-MS (m/z): 316 (M+1)$^+$.

Example 25

Preparation of Compound of Formula IIIF

A stirred solution of compound of Formula BF (1 eq) in Toluene (5 Vol) was cooled to 0-5° C. Thionyl chloride was added slowly at 0-5° C. over a period of 10 min. Reaction was stirred at RT for 30 min. Progress of the reaction was monitored by TLC, acid chloride was formed. In another RBF, 2, 4-difluoro benzyl amine (1 eq) in toluene (5 Vol) and trimethyl amine (3 eq) were taken at RT. Above formed acid chloride was added slowly to the RM at 5-10° C. Reaction mass was stirred at RT for 2 h. Progress of the reaction was monitored by TLC. After complete reaction, water was added to the reaction mass, layer separated and aq. layer was extracted with toluene. Combined all the organic layers and was washed with 2N HCl followed by saturated sodium bicarbonate solution. Organic layer dried over anhydrous $Na_2SO_4$, filtered off and distilled to obtain compound of Formula IIIF (60% yield). $^1$H NMR (300 MHz, $CDCl_3$): 7.27-7.38 (m, 1H), 6.7-6.86 (m, 2H), 4.42-4.44 (d, 2H), 3.89-4.0 (m, 4H), 3.36-3.57 (m, 4H), 2.68 (s, 2H), 1.62-1.67 (m, 1H), 1.39-1.46 (m, 2H), 0.85-0.90 (d, 6H). ESI-MS (m/z): 358 (M+1)$^+$.

Example 26

Preparation of Compound of Formula IVA 4N hydrochloric acid (1.5 Lt, 10 V/W) was added to the compound of Formula IIIA (wherein R=benzyl, $P_1$ & $P_2$ together form 1,3-dioxolane ring, 150 g) in acetone (1.5 Lt, 10 V/W) at 20-25° C. and the reaction mass was heated to 60-65° C. then stirred for 5 hrs. Upon completion, the reaction mass was cooled to room temperature and acetone was distilled off completely under vacuum. The obtained crude compound was dissolved in water (1.5 Lt, 10V) and then extracted with ethyl acetate (15V). Organic layer was separated and washed with saturated sodium bicarbonate solution (5V) followed by water (5V) and brine (5V) solution. Organic layer was dried over anhydrous sodium sulfate and the solvent was distilled off completely under vacuum. The obtained crude was cooled to −30 to −35° C. and heptane (750 mL, 5V) was added to it then stirred. The obtained solid was filtered off to get the title compound as off-white low melting solid (124 g, 94% Yield). MS (ES): m/z 334 (M+H)$^+$.

Example 27

Preparation of Compound of Formula IVB 4N hydrochloric acid (70 mL, 10 V/W) was added to the compound of Formula IIIB (wherein R=ethyl, $P_1$ & $P_2$ together form 1,3-dioxolane ring, 7 g) in acetone (70 mL, 10V) at 20-25° C. and reaction mass was heated to 60-65° C. then stirred for about 6 hrs. Upon completion, the reaction mass was cooled to room temperature and acetone was distilled off completely under vacuum. The obtained crude compound was dissolved in water (100 mL) and then extracted with ethyl acetate (15V). Organic layer was separated and was washed with saturated sodium bicarbonate solution (5V) followed by water (5V) and brine (5V) solution. Organic layer was dried over anhydrous sodium sulfate and the solvent was distilled off completely under vacuum to get title compound as light brown oily liquid (5.4 g, 88% Yield). MS (ES): m/z 272 (M+H)$^+$.

Example 28

Preparation of Compound of Formula IVB

Aqueous hydrochloric acid 20% (1 Lt, 5V) was added to a solution of compound of Formula IIIB (wherein R=ethyl; $P_1$ & $P_2$ together form 1,3-dioxolane ring, 200 g, 1 eq) in toluene (1 Lt, 5V) followed by TBAB (2 g, 0.01 eq) at 20-25° C. The reaction mass was heated to 95-100° C. and stirred for 5 hrs. After reaction completion, the reaction mass was cooled to room temperature. Organic layer was separated and the aqueous layer was extracted with ethyl acetate (2×5V). Organic layer was washed with saturated sodium bicarbonate solution (5V) followed by water (5V) and brine (5V) solution. Organic layer was dried over anhydrous sodium sulfate and then distilled off to get the crude. Diisopropyl ether (2V) was added to the crude, heated to reflux to get the clear solution and then cooled to room temperature. Heptane (3V) was added to the reaction mass and stirred for 30 min. The resulting solid was filtered, washed with diisopropyl ether/heptane mixture (1:2, 2V) and dried to get the pure title compound as solid (122 g, 71% Yield). MS (ES): m/z 272 (M+H)$^+$.

In another experiment, to a stirred solution of compound of Formula IIIC (1 eq) in toluene (10 Vol) was added 2N HCl (10 Vol) at RT. Temperature of the reaction mass was raised to 85-90° C. and maintained for 5 h. Progress of the reaction was monitored by TLC, after complete reaction, organic layer separated and aq. layer was extracted with toluene. Combined the organic layer and was washed with saturated sodium bicarbonate solution. Organic layer was dried over $Na_2SO_4$ and then distilled of solvent to obtain crude compound 6. Crude compound was purified by using diisopropyl ether (5V) and compound of Formula IVB was isolated as off white solid (65% yield). $^1$H NMR (300 MHz, $CDCl_3$): 7.28-7.33 (m, 1H), 6.77-6.87 (m, 2H), 4.45 (d, 2H), 4.11 (s, 2H), 3.57 (q, 2H), 3.50 (s, 2H), 1.23 (t, 3H). ESI-MS (m/z): 272 (M+1)$^+$.

Example 29

Preparation of Compound of Formula IVC

To a stirred solution of Compound of Formula IIID (1 eq) in toluene (10 Vol), 2N HCl (10 Vol) was added at RT. Temperature of the reaction mass was raised to 85-90° C.

and maintained for 5 h. Progress of the reaction was monitored by TLC, after complete reaction, organic layer separated and aq. layer was extracted with toluene. Combined all the organic layers and was washed with saturated sodium bicarbonate solution. Organic layer was dried over $Na_2SO_4$ and distilled the solvent to obtain crude compound of Formula IVC. Crude compound was purified by using diisopropyl ether (5V) and compound of Formula IVC was isolated as off white solid (66% yield). $^1$H NMR (300 MHz, $CDCl_3$): 7.28-7.36 (m, 1H), 6.77-6.87 (m, 2H), 4.45 (d, 2H), 4.09 (s, 2H), 3.47 (s, 2H), 3.41 (s, 3H). ESI-MS (m/z): 258 $(M+1)^+$.

In a similar reaction, to a stirred solution of compound of Formula IIIE (1 eq) in toluene (10 Vol), 2N HCl (10 Vol) was added at RT. Temperature of the reaction mass was raised to 85-90° C. and maintained for 5 h. Progress of the reaction was monitored by TLC, after complete reaction, organic layer separated and aq. layer was extracted with toluene. Combined organic layers and was washed with saturated sodium bicarbonate solution. Organic layer was dried over $Na_2SO_4$ and then distilled to obtain crude compound of Formula IVC. Crude compound was purified by using diisopropyl ether (5V) and compound of Formula IVC was isolated as off white solid (62% yield).

Example 30

Preparation of Compound of Formula IVD

To a stirred solution of compound of Formula IIIF (1 eq) in toluene (10 Vol) was added 2N HCl (10 Vol) at RT. Temperature of the reaction mass was raised to 85-90° C. and maintained for 5 h. Progress of the reaction was monitored by TLC, after complete reaction, organic layer separated and aq. layer was extracted with toluene. Combined the organic layer and was washed with saturated sodium bicarbonate solution. Organic layer was dried over $Na_2SO_4$ and distilled to obtain crude compound of Formula IVD. Crude compound was purified by using Diisopropyl ether (5V) and compound of Formula IVD was isolated as off white solid (65% yield). $^1$H NMR (300 MHz, $CDCl_3$): 7.27-7.33 (m, 1H), 6.7-6.86 (m, 2H), 4.44-4.46 (d, 2H), 4.07-4.09 (d, 2H), 3.47-3.52 (m, 4H), 1.65-1.72 (m, 1H), 1.45-1.5 (m, 2H), 0.86-0.90 (d, 6H). ESI-MS (m/z): 314 $(M+1)^+$.

Example 31

Preparation of Compound of Formula VIIA

N,N-dimethyl-1,1-bis(methyloxy)methanamine (4.2 mL, 2 eq) was added to the compound of Formula IVA (5 g) in toluene (50 mL, 10V) at 0-5° C. and the reaction mass was stirred for 3 hrs at room temperature. After reaction completion, the reaction mass was cooled 0-5° C. and aminoacetaldehyde-dimethylacetal (2.4 mL, 1.5 eq) was added. The reaction mass was stirred at room temperature for 30 min and poured into ice cold water (50 mL, 10V). Toluene layer was separated and aqueous layer was extracted with ethyl acetate (2×5V). Organic layer was separated and washed with water (5V) followed by brine (5V) solution. Organic layer was dried over anhydrous sodium sulfate and the solvent was distilled off completely to get the title compound as brown colour oily liquid (6 g, 90% Yield). MS (ES): m/z 449 $(M+H)^+$.

Example 32

Preparation of Compound of Formula VIM

N,N-dimethyl-1,1-bis(methyloxy)methanamine (5.6 mL, 2 eq) was added to the compound of Formula IVB (wherein R=ethyl, 5.4 g, 1 eq) in dimethylformamide (27 mL, 5V) at 0-5° C. and was stirred for 3 hrs at room temperature. The reaction mass was heated to 50-55° C. and stirred for 30 min. After reaction completion, the reaction mass was cooled 0-5° C. and aminoacetaldehyde dimethylacetal (3.2 mL, 1.5 eq) was added. The reaction mass was stirred for 30 min at room temperature and poured into ice cold water (50 mL, 10V) and then extracted with ethyl acetate (2×10V). Organic layer was separated and washed with water (5V) followed by brine (5V) solution. Organic layer was dried over anhydrous sodium sulfate and solvent was distilled off completely to get the title compound as brown colour oily liquid (4.8 g, 62% Yield). MS (ES): m/z 387 $(M+H)^+$.

Example 33

Preparation of Compound of Formula VIM

N,N-di methyl-1,1-bis(m ethyl oxy)methanamine (DMF-DMA) (32.9 g, 3 eq) was added to the compound of Formula IVB (25 g) in toluene (250 ml, 10V) at 0-5° C. The temperature of the reaction mass was allowed to attain the room temperature and stirred for 4 hrs. After reaction completion, the reaction mass was cooled to 0-5° C. Aminoacetaldehde dimethylacetal (15 ml, 1.5 eq) was added to the reaction mass and stirred for 24 hrs at room temperature. After reaction completion, the reaction mass was poured into water (20V) and then extracted with toluene (2×10V). Organic layer was separated and washed with 1N hydrochloric acid (5V) followed by brine (5V) solution. Organic layer was dried over anhydrous sodium sulfate and the solvent was distilled off completely to get the title compound as brown colour oil (30.3 g, 85% Yield). MS (ES): m/z 387 $(M+H)^+$.

Example 34

Preparation of Compound of Formula VIIC

To a stirred solution of Compound of Formula IVC (1 eq) in toluene (10 Vol), DMF.DMA (3 eq) was added at RT. Reaction mass was stirred at RT for 5 h. Progress of the reaction was monitored by TLC. After complete reaction, amino acetaldehyde dimethyl acetal (1.5 eq) was added at RT. Reaction was stirred at RT for 15 h. Progress of the reaction was monitored by TLC. After complete reaction, ice cold water was added to the reaction mass, organic layer separated and aq. layer was extracted with toluene. Combined the organic layers and was washed with 0.5 N HCl followed by saturated sodium bicarbonate solution. Organic layer was dried over $Na_2SO_4$ and distilled to obtain crude compound of Formula VIIC. Crude compound was purified by using silica gel column chromatography with a gradient of 20-25% EtOAc in hexanes and isolated compound of Formula VIIC (68% yield). $^1$H NMR (300 MHz, $CDCl_3$): 8.07 (d, 1H), 7.26-7.37 (m, 1H), 6.78-6.87 (m, 2H), 4.54 (d, 2H), 4.45 (t, 1H), 4.24 (s, 2H), 3.46 (s, 3H), 3.44 (d, 2H), 3.43 (s, 6H). ESI-MS (m/z): 373 $(M+1)^+$.

Example 35

Preparation of Compound of Formula VIID

To a stirred solution of compound of Formula IVD (1 eq) in toluene (10 Vol), DMF.DMA (3 eq) was added at RT. Reaction mass was stirred at RT for 5 h. Progress of the reaction was monitored by TLC. After complete reaction, amino acetaldehyde dimethyl acetal (1.5 eq) was added at RT. Reaction was stirred at RT for 15 h. Progress of the reaction was monitored by TLC. After complete reaction, ice cold water was added to the reaction mass, organic layer separated and aq. layer was extracted with toluene. Combined the organic layers and was washed with 0.5 N HCl followed by saturated sodium bicarbonate solution. Organic layer was dried over $Na_2SO_4$ and distilled to obtain crude compound of Formula IVD. Crude compound was purified by using silica gel column chromatography with a gradient of 20-25% EtOAc in hexanes and isolated compound of Formula VIID (68% yield). $^1$H NMR (300 MHz, $CDCl_3$): 8.11-8.15 (d, 1H), 7.23-7.34 (m, 1H), 6.74-6.84 (m, 2H), 4.5-4.52 (d, 2H), 4.39-4.42 (t, 1H), 4.22 (s, 2H), 3.47-3.51 (m, 2H), 3.38-3.42 (m, 8H), 1.66-1.68 (m, 1H), 1.44-1.51 (m, 2H), 0.84-0.9 (d, 6H). ESI-MS (m/z): 511 $(M+1)^+$.

Example 36

Preparation of Compound of Formula IXA

Sodium tert-pentoxide (120 g, 4 eq) was added to the compound of Formula VILA (wherein R=benzyl; $R_1$ & $R_2$=methyl, 120 g, 1 eq) in diethyl oxalate (250 mL, 5V) at 0-5° C. The reaction mass was heated to 70-80° C. and stirred for 15-20 min. After reaction completion, the reaction mass was poured in to water (1.2 Lt, 10V) and pH of the reaction mass was adjusted to ~4 to 5 by using 4N hydrochloric acid. The reaction mass was extracted with ethyl acetate (15V). Organic layer was separated, washed with saturated bicarbonate solution (5V), water followed by brine (5V) solution. Organic layer was dried over anhydrous sodium sulfate and the solvent was distilled off completely under vacuum. The obtained crude compound was purified by silica gel column chromatography (Eluent: EtOAc-hexane). Pure fractions were collected and distilled off to get the title compound as brown oily liquid (62 g, 49.6%). MS (ES): m/z 469 $(M+H)^+$.

Example 37

Preparation of Compound of Formula IXB

Sodium tert-pentoxide (4 g, 4 eq) was added to the compound of Formula VIIB (wherein R=ethyl; $R_1$ & $R_2$=methyl, 3.5 g, 1 eq) in diethyl oxalate (17.5 mL, 5V) at 5-10° C. The reaction mass was heated to 110-120° C. and stirred for an hour. After reaction completion, the reaction mass was poured in to water (10V) and extracted with ethyl acetate (2×5V). Organic layer was separated and washed with saturated bicarbonate solution (5V), water (5V) followed by brine solution. Organic layer was dried over anhydrous sodium sulfate and the solvent was distilled off completely under vacuum. Thus obtained crude compound was purified by silica gel column chromatography (Eluent: EtOAc-hexane). Pure fractions were collected and distilled off to get the title compound as brown oily liquid (1.7 g, 40% Yield). MS (ES): m/z 469 $(M+H)^+$.

Example 38

Preparation of Compound of Formula IXB

A mixture of compound of Formula VIIB (wherein R=ethyl; $R_1$ & $R_2$=methyl, 100 g), diethyl oxalate (300 mL, 3V), Sodium ethoxide (44.5 g, 2.5 eq) and toluene (5V) was heated to 80-85° C. and stirred for 2-3 hrs. After reaction completion, the reaction mass was cooled to room temperature and water (20V) was added to it. The organic and aqueous layers were separated. Aqueous layer was extracted with toluene (2×5V). The organic layers were combined and washed with saturated sodium bicarbonate solution (5V) followed by water (5V) and brine (5V) solution. Organic layer was distilled off completely under vacuum to get the title compound as brown colour liquid. Crude wt: 145 g (100%). MS (ES): m/z 469 $(M+H)^+$.

In a similar reaction, a mixture of compound of Formula VIIB (wherein R=ethyl), diethyl oxalate (1V), Sodium ethoxide (2.5 eq) and toluene (15V) was heated to 50-55° C. and stirred for 2-3 hrs. After reaction completion, reaction mass was cooled to room temperature and water (20V) was added to it. The organic and aqueous layer was separated. Aqueous layer was extracted with toluene (2×5V). The organic layers was combined and washed with 1N HCl (5 V) and saturated sodium bicarbonate solution (5V). Organic layer was completely distilled off under vacuum to get the title compound as brown colour liquid (75% Yields) MS (ES): m/z 469 $(M+H)^+$.

Example 39

Preparation of Compound of Formula IXB

To a stirred solution of Compound of Formula VIIC (1 eq) in toluene (10 Vol), sodium ethoxide (2.5 eq) was added at RT followed by diethyl oxalate (1 Vol). Reaction mass was stirred at 50-55° C. for 4 h. Progress of the reaction was monitored by TLC. After complete reaction, reaction mass was cooled to RT and water was added. Organic layer separated and aq. layer was extracted with toluene. Combined the organic layers and was washed with 1 N HCl followed by saturated sodium bicarbonate solution. Organic layer was dried over $Na_2SO_4$ and then distilled of solvent to obtain crude compound of Formula IXC. Crude compound was purified by using silica gel column chromatography with a gradient of 25-30% EtOAc in hexanes and isolated compound of Formula IXB (50% yield). $^1$H NMR (300 MHz, $CDCl_3$): 10.4 (s, 1H), 8.41 (s, 1H), 7.36-7.38 (m, 1H), 6.76-6.84 (m, 2H), 4.62 (d, 2H), 4.52 (t, 1H), 4.47 (q, 2H), 4.25 (q, 2H), 4.02 (d, 2H), 3.39 (s, 6H), 1.42 (t, 3H), 1.33 (t, 3H). ESI-MS (m/z): 469 $(M+1)^+$.

Example 40

Preparation of Compound of Formula IXB

To a stirred solution of compound of Formula VIID (1 eq) in toluene (10 Vol), sodium ethoxide (2.5 eq) was added at RT followed by diethyl oxalate (1 Vol). Reaction mass was stirred at 50-55° C. for 4 h. Progress of the reaction was monitored by TLC. After complete reaction, reaction mass was cooled to RT and water was added. Organic layer separated and aq. layer was extracted with toluene. Combined the organic layers and was washed with 1 N HCl followed by saturated sodium bicarbonate solution. Organic layer was dried over Na2SO4 and then distilled of solvent to obtain crude compound 7. Crude compound was purified by using silica gel column chromatography with a gradient of 25-30% EtOAc in hexanes and isolated compound of Formula IXB (50% yield). $^1$H NMR (300 MHz, $CDCl_3$): 10.4 (s, 1H), 8.41 (s, 1H), 7.36-7.38 (m, 1H), 6.76-6.84 (m, 2H), 4.62 (d, 2H), 4.52 (t, 1H), 4.47 (q, 2H), 4.25 (q, 2H), 4.02 (d, 2H), 3.39 (s, 6H), 1.42 (t, 3H), 1.33 (t, 3H). ESI-MS (m/z): 469 $(M+1)^+$.

Example 41

Preparation of Compound of Formula IXC

A mixture of compound of Formula VIIB, dimethyl oxalate (3 eq), Sodium methoxide (2.5 eq) and toluene (15V) was heated to 50-55° C. and stirred for 4-5 hrs. After complete reaction, mass was cooled to room temperature and water (20V) was added to it. The organic and aqueous layer was separated. Aqueous layer was extracted with toluene (2×5V). The organic layers was combined and washed with 1N HCl (5 V) and saturated sodium bicarbonate solution (5V). Organic layer was completely distilled off under vacuum to get the title compound (Formula IXC) as brown colour liquid (75% Yields). $^1$H NMR (300 MHz, CDCl$_3$): 10.28-10.31 (t, 1H), 8.47 (s, 1H), 7.4-7.6 (m, 1H), 7.2-7.38 (m, 2H), 4.53-4.55 (d, 2H), 4.2-4.24 (m, 1H), 3.9 (s, 3H), 3.7 (s, 3H), 3.3 (s, 6H), 3.33 (d, 2H). MS (ES): m/z 441 (M+H)$^+$.

Example 42

Preparation of Compound of Formula IXB

To a stirred solution of Compound of Formula VIIB (1 eq) in toluene (10 Vol), sodium ethoxide (2.5 eq) was added at RT followed by diethyl oxalate (1 Vol). Reaction mass was stirred at 50-55° C. for 4 h. Progress of the reaction was monitored by TLC. After complete reaction, reaction mass was cooled to RT and water was added. Organic layer separated and aq. layer was extracted with toluene. Combined the organic layers and was washed with 1 N HCl followed by saturated sodium bicarbonate solution. Organic layer was dried over Na$_2$SO$_4$ and then distilled of solvent to obtain crude compound. The obtained crude compound was purified by using silica gel column chromatography with a gradient of 25-30% EtOAc in hexanes and isolated title compound (50% yield). $^1$H NMR (300 MHz, CDCl$_3$): 10.4 (s, 1H), 8.41 (s, 1H), 7.36-7.38 (m, 1H), 6.76-6.84 (m, 2H), 4.62 (d, 2H), 4.52 (t, 1H), 4.47 (q, 2H), 4.25 (q, 2H), 4.02 (d, 2H), 3.39 (s, 6H), 1.42 (t, 3H), 1.33 (t, 3H). ESI-MS (m/z): 469 (M+1)$^+$.

Example 43

Preparation of Compound of Formula XB

Mixture of compound of Formula IXB (wherein R & R$_4$=ethyl; R$_1$ & R$_2$=methyl) (100 g) and formic acid (10V) was heated to 80-85° C. and stirred for 3 hrs. After reaction completion, the reaction mass was cooled to room temperature and water (20V) was slowly added to it then stirred for 30 min. The obtained solid was filtered off and washed with water (10V). The solid was slurry washed with diisopropylethether (5V), filtered and dried to get the title compound (62 g, 56% Yield). MS (ES): m/z 423 (M+H)$^+$.

In a similar reaction, a mixture of compound of Formula IXB (wherein R is ethyl) (1 eq) and formic acid (5 v) was heated to 75-80° C. and stirred for 3 hrs. After reaction completion, the reaction mass was cooled to room temperature and water (25 vol) was slowly added to it then stirred for 30 min. The obtained solid was filtered off and washed with water (10V). The solid was slurry washed with diisopropylethether (5V), filtered and dried to get the title compound (56% Yield). MS (ES): m/z 423 (M+H)$^+$.

Example 44

Preparation of Compound of Formula XIB

R-3-amino 1-butanol (69 mg, 1.2 eq) in methanol (0.08 mL, 3 eq) was added to the compound of Formula XB (wherein R & R$_4$=ethyl) (0.27 g, 1 eq) in toluene (3 mL, 10V) followed by acetic acid (0.04 mL, 1.2 eq) at room temperature. The reaction mass was heated to 85-90° C. and stirred for 24 hrs. After reaction completion, the reaction mass was cooled to room temperature and poured into water. The reaction mass was extracted with ethyl acetate and the separated organic layer was washed with saturated bicarbonate solution followed by water and brine solution. Organic layer was dried over anhydrous sodium sulfate and distilled off completely. The obtained crude compound was purified on neutral alumina column chromatography (Eluent: MeOH-DCM) and pure fractions were distilled to get the title compound (0.2 g, 71%). MS (ES): m/z 448 (M+H)$^+$.

Example 45

Preparation of Compound of Formula XIB

R-3-amino 1-butanol (6.4 g, 1.2 eq), methanol (7.2 ml, 3 eq) and acetic acid (7.4 ml, 2.2 eq) was added to the compound of Formula XB (wherein R & R$_4$=ethyl) (25 g, 1 eq) in toluene (250 ml, 10V) at room temperature. The reaction mass was heated to 85-90° C. and stirred for 36 hrs. After reaction completion, the reaction mass was cooled to room temperature and poured into water (5V). Toluene layer was separated and aqueous layer was extracted with toluene (2×5V). Combined organic layer was washed with saturated sodium bicarbonate solution (5V), water (5V) followed by brine solution. The separated organic layer was dried over anhydrous sodium sulfate and distilled off the solvent. Thus obtained crude was purified by recrystallization from ethyl acetate (2V) to get the title compound as off white solid (17.2 g, 65% Yield). Purity by HPLC: 99.80%, MS (ES): m/z 448 (M+H)$^+$.

Example 46

Preparation of Dolutegravir

Aqueous sodium hydroxide solution (3 eq, 53 mg in 0.66 mL of water) was added to compound of Formula XIB (wherein R=ethyl) (200 mg, 1 eq) in ethanol (2 mL, 10V) at 20-25° C. The reaction mass was heated to 90-100° C. and stirred for 10 hrs. After reaction completion, the reaction mass was filtered and water (10V) was added to the obtained solid. pH of the reaction mass was adjusted to ~4 by using dilute hydrochloric acid then stirred for 15 min at 20-25° C. The solid obtained was filtered and washed with water. Finally the compound was triturated with diisopropylether (10V) to get the title compound (120 mg, 66%). Purity by HPLC: 88%, MS (ES): m/z 420 (M+H)$^+$.

Example 47

Preparation of Sodium Salt of Dolutegravir

Dolutegravir (1 g) was dissolved in ethanol (10 mL, 10V) at 85-90° C. and filtered in hot condition through 0.2 micron filter paper. 2N sodium hydroxide solution (1 eq, 95 mg in 1.2 mL of DM water) was added to the filtrate at 85-90° C. and stirred for 30 min. The reaction mass was cooled to room temperature and the solid obtained was filtered, washed with ethanol (5V) and dried under vacuum at 35-40° C. for 30 min to get Dolutegravir sodium salt as yellow colour solid (830 mg). HPLC Purity: 88%.

Example 48

Preparation of Sodium Salt of Dolutegravir

Sodium hydroxide powder (8.94 g, 10 eq) was added to the compound of Formula XIB (wherein R=ethyl) (10 g, 1 eq) in ethanol (50 mL, 5V) and DMSO (25 ml, 2.5 V) at 20-25° C. and stirred for 5-6 hrs. After reaction completion, the reaction mass was filtered and washed with ethanol (2V).

The obtained solid was suck dried and acidified with aqueous hydrochloric acid at 0-5° C. The solid formed was filtered off, washed with water (5V) and suck dried under vacuum for 10 min. The resulting solid was dried under vacuum at 50-55° C. for 1 h (7.5 g). Ethanol (10V) was added to the obtained solid and heated to 80-85° C. 2N sodium hydroxide solution (1 eq, 714 mg dissolved in 8.9 mL water) was added to the reaction mass at 80-85° C. and stirred for 10-20 min. The reaction mass was cooled to 20-25° C. The solid obtained was filtered off, washed with ethanol then dried under vacuum to get the title compound (7 g, 71% Yield). Purity by HPLC: 99.83%

Example 49

Preparation of Sodium Salt of Dolutegravir

The title compound was prepared in a similar manner to Example 48, but using tetrahydrofuran as a solvent in place of DMSO. Purity by HPLC: 99.78%.

Example 50

Preparation of Sodium Salt of Dolutegravir using Methanol

To a stirred solution of compound of Formula XIB (1 eq) in DMSO (2.5 Vol) and methanol (5 v) was cooled to 10-15° C. Powdered sodium hydroxide was added slowly at 10-15° C. Reaction was stirred at RT for 2-3 h. Progress of the reaction was monitored by TLC, after complete reaction, RM was cooled to 0-5° C. Filtered the solid, added water and cooled to 0-5° C. Reaction mass pH was adjusted to 3-4 by using 2N HCl and compound was extracted with DCM. Organic layer was dried over $Na_2SO_4$ and distilled to obtain Dolutegravir (70% yield).

To a stirred solution of Dolutegravir (1 eq) in methanol (10 v) at 70-75° C., was added 2N sodium hydroxide (1 eq) slowly and was slowly cooled to RT. Filtered the solid, washed with methanol (7 v) and dried to get title compound with 99.49% purity by HPLC (70% yield).

Figure 6:
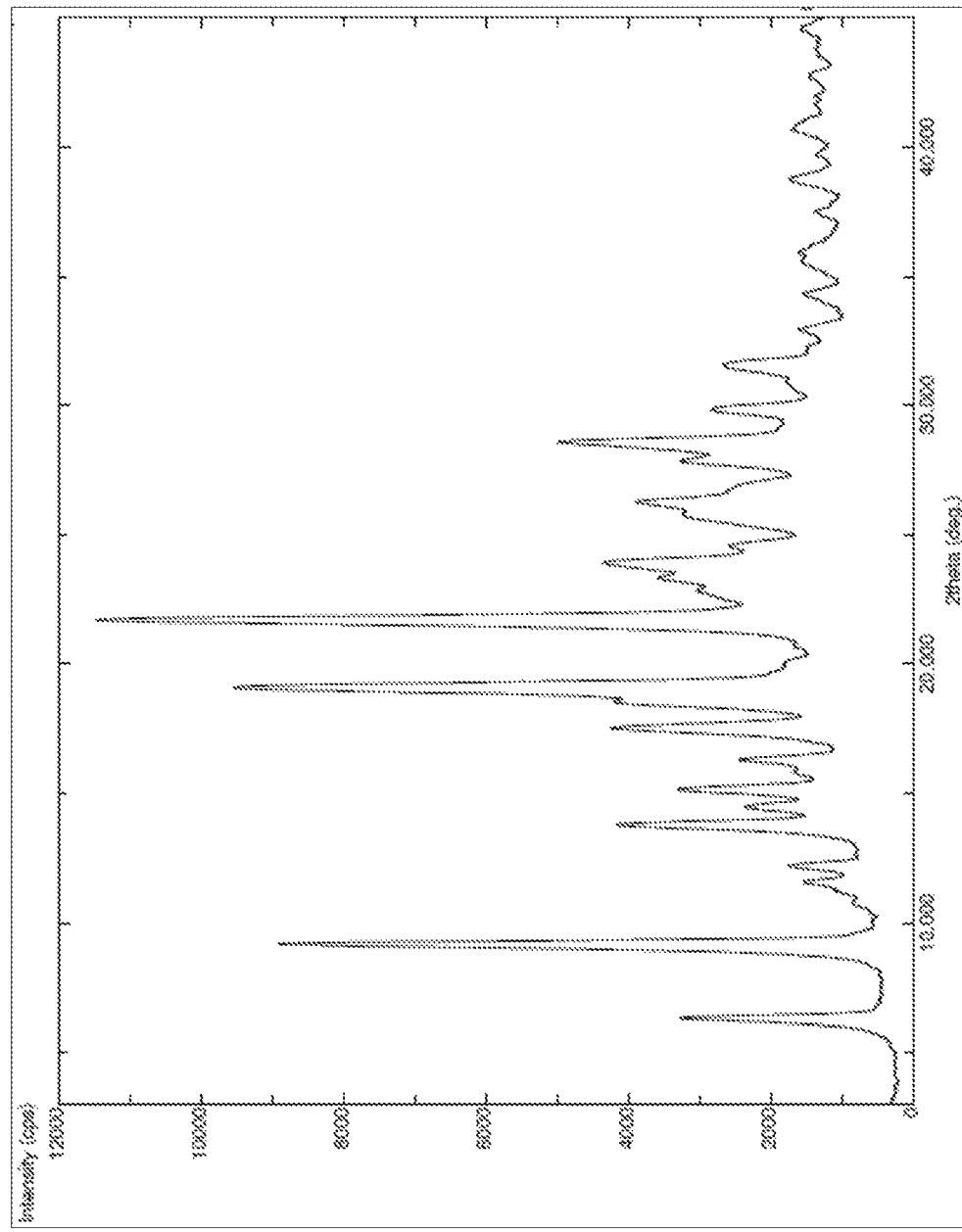
FIG. 6 is the PXRD spectrum of the sodium salt of dolutegravir prepared according to Example 50.

The PXRD spectra are shown in FIG. 6

Example 51

Preparation of Sodium Salt of Dolutegravir Using Isopropanol

To a stirred solution of compound of Formula XIB (1 eq) in DMSO (2.5 Vol) and isopropanol (5 v) was cooled to 10-15° C. Powdered sodium hydroxide was added slowly at 10-15° C. Reaction was stirred at RT for 2-3 h. Progress of the reaction was monitored by TLC, after complete reaction, RM was cooled to 0-5° C. Filtered the solid, added water and cooled to 0-5° C. Reaction mass pH was adjusted to 3-4 by using 2N HCl and compound was extracted with DCM. Organic layer was dried over $Na_2SO_4$ and distilled to obtain compound Dolutegravir (70% yield).

To a stirred solution of Dolutegravir (1 eq) in isopropanol (10 v) at 70-75° C., was added 2N sodium hydroxide (1 eq) slowly and was slowly cooled to RT. Filtered the solid, washed with isopropanol (7 v) and dried to get compound of Formula I-Na with 99.3% purity by HPLC (70% yield).

Example 52

Preparation of Potassium Salt of Dolutegravir

To a stirred solution of Dolutegravir (1 eq) in ethanol (10 v) at 70-75° C., was added 2N potassium hydroxide (1 eq) solution slowly and at 70-75° C. and slowly cooled to RT. Filtered the solid, washed with ethanol (7 v) and dried to get Dolutegravir potassium salt with 99.6% purity by HPLC (70% yield).

The PXRD spectra are shown in FIG. 7

Example 53

Preparation of Calcium Salt of Dolutegravir

To a stirred solution of Dolutegravir (1 eq) in ethanol (7 v) and the aqueous calcium chloride (0.52 eq) solution was added to the reaction mass over a period of 10-15 min while maintaining temp of 35-40° C. Maintain the reaction mass at 25-30° C. for 24 h. Filtered the solid, washed with ethanol (7 v) and dried to get Dolutegravir calcium salt (60% yield).

The PXRD spectra are shown in FIG. 8

Example 54

Preparation of Sodium Salt of Dolutegravir using DCM/EtOH

Sodium hydroxide (7.0 eq) was added in to ethanol (5 v) and stirred for 1 hr at room temperature, then reaction mass was cooled to 10-15° C. Compound of Formula XIB (1 eq) in DCM (7.0 Vol) was added to reaction mass at 10-15° C. then reaction mass temp was raised to room temperature and stirred for 10 h. Progress of the reaction was monitored by HPLC. Upon completion, reaction mass was diluted with DCM (13V) and water (5V) and reaction mass was cooled to 0-5° C. Reaction mass pH was adjusted to 2-3 by using with 2N HC (8V), separated both layers, aqueous layer was extracted with DCM and washed with aqueous sat. $NaHCO_3$ soln. followed by brine wash, separate the DCM layer and concentrated at 40-45° C. and Co-distill with ethanol under vacuum at below 50° C. Resulting reaction mass was purified by slurry wash with Ethanol (3V) at reflux condition, then cooled to room temperature, filtered and cake washed with ethanol and suck dried for 30 min to get compound I. Resulting compound I and ethanol (3V) were taken in to a RBF at room temperature and heated to reflux and then added 2N NaOH soln. (1V) at reflux temperature and reaction mass was gradually cooled to room temperature. The solid was filtered, washed with ethanol (3V), and dried under vacuum. The sodium salt of dolutegravir was obtained (85% yield).

Example 55

General X-Ray Powder Diffraction Method

X-ray: Cu/30 kV/15 mA; Goniometer: MiniFlex 2; Attachment: Standard sample holder; Filter: not used; I. Monochro: not used; C. Monochro: not used; Div Slit: 1.25 deg; Rec Slit: 0.3 mm; Sct Slit: 1.25 deg; Counter: MiniFlex 2; Scan mode: Continuous; Scan speed: 5.000 deg/min; Sampling width: 0.020 deg; Scan axis: 2 theta/theta; Scan range: 3.000 to 45.000 deg; theta offset: 0.000 deg.

We claim:

1. A compound of Formula III, wherein R is one of an alkyl, an aryl and an aralkyl, and each of $P_1$ and $P_2$ is, independently, a ketal protecting group or together form a cyclic ring Formula III

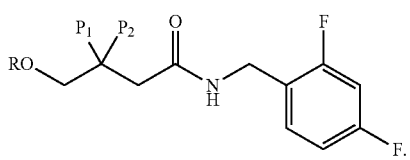

2. A compound of Formula IV, wherein R is one of an alkyl, an aryl and an aralkyl Formula IV

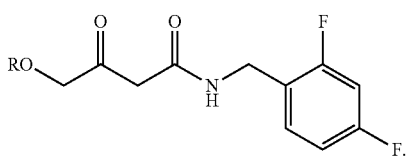

3. A compound of Formula V, wherein R is one of an alkyl, an aryl and an aralkyl Formula V

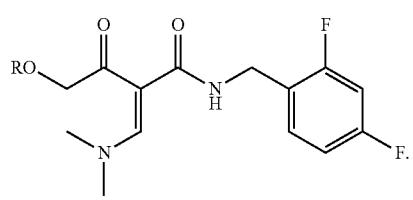

4. A compound of Formula VII, wherein R is one of an alkyl, an aryl and an aralkyl, and each of $R_1$ and $R_2$ is, independently, an alkyl Formula VII

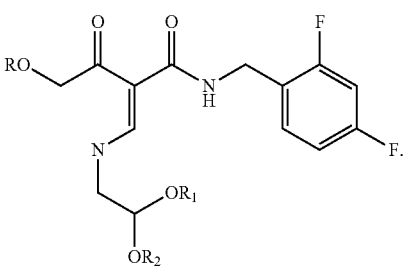

5. The compound according to claim 1, wherein R is one of a methyl, an ethyl, an isoamyl, and a benzyl, and wherein when $P_1$ and $P_2$ together form a cyclic ring the cyclic ring comprising one of ethylene glycol and propane diol.

6. A method of preparing a compound of Formula III,

Formula III

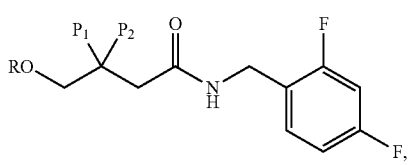

comprising reacting 2,4-difluoro benzylamine with a compound of Formula II or a reactive derivative thereof, Formula II

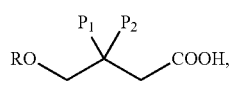

to produce the compound of Formula III, wherein R is one of an alkyl, an aryl and an aralkyl group, and wherein each of $P_1$ and $P_2$ is, independently, a ketal protecting group or together form a cyclic ring.

7. The method of claim 6, wherein the reaction of the compound of Formula II with 2,4-difluorobenzylamine is carried out in the presence of a base, an acid chloride forming agent or coupling agent, and optionally a solvent.

8. The method of claim 7, wherein,
the acid chloride forming agent is selected from one of ethyl chloroformate, isobutyl chloroformate, isopropenyl chloroformate and thionylchloride;
the coupling agent is selected from one of cabonyldiimidazole, carbonyl-di(1,2,4-triazole),1-ethyl-3-(3-dimethylaminopropyl)carbodiimide, N,N'-diisopropyl carbodiimide, and dicyclohexyl carbodiimide;
the base is selected from one of N-methylmorpholine, triethylamine, trimethylamine and diisopropylethylamine; and
the optional solvent is selected from one of a nitrile, an ether, a chloro solvent, a hydrocarbon, an ester, an amide, and mixtures thereof.

9. The compound according to claim 2, wherein R is one of a methyl, an ethyl, an isoamyl, and a benzyl.

10. A method of preparing a compound of Formula IV,

Formula IV

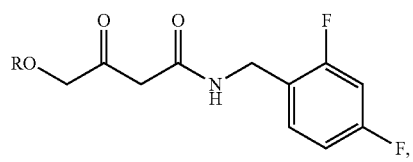

comprising deprotecting a compound of Formula III,

Formula III

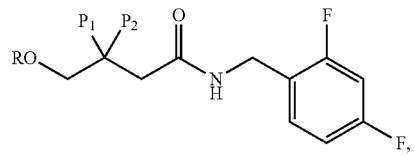

to produce a compound of Formula IV, wherein R is one of an alkyl, an aryl and an aralkyl group, and each of $P_1$ and $P_2$ is, independently, a ketal protecting group or together form a cyclic ring.

11. The method of claim 10, wherein the deprotection step is carried out in the presence of an acid, a solvent, and optionally a phase transfer catalyst.

12. The method of claim 11, wherein,
the acid is selected from one of hydrochloric acid, hydrobromic acid, acetic acid, sulfuric acid, p-toluene sulfonic acid, methane sulfonic acid, and mixtures thereof;
the solvent is selected from one of an ether, a ketone, a hydrocarbon, an ester, and mixtures thereof, and the optional phase transfer catalyst is selected from one of tetra butyl ammonium bromide, tetra butyl ammonium iodide, tetra butyl ammonium chloride, tetra butyl ammonium tribromide, tetra butyl phosphonium bromide, triethylbenzyl ammonium chloride, tetra methyl ammonium iodide, tetra butyl ammonium acetate, Aliquat-336, or tetra butyl ammonium fluoride.

13. The method of claim 11, wherein the acid is hydrochloric acid, the solvent is one or toluene or acetone, and the optional phase transfer catalyst is tetra butyl ammonium bromide.

14. The compound according to claim 3, wherein R is one of a methyl, an ethyl, an isoamyl, and a benzyl.

15. A method of preparing a compound of Formula V,

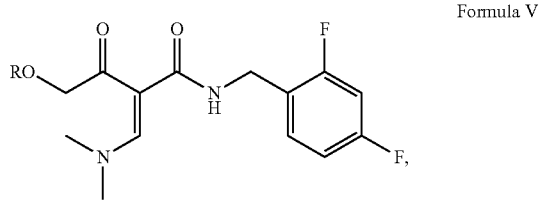

Formula V comprising treating the compound of Formula IV,

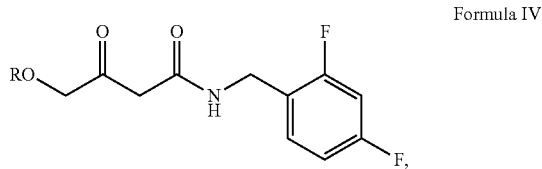

Formula IV with N,N-dimethyl-1,1-bis(methyloxy) methanamine to produce the compound of Formula V, wherein R is one of an alkyl, an aryl and an aralkyl group.

16. The method of claim 15, wherein the reaction of compound of Formula IV with N,N-dimethyl-1,1-bis(methyloxy) methanamine is carried out in the presence of a solvent selected from one of an alcohol, an ether, a hydrocarbon, an amide, and mixtures thereof.

17. The method of claim 16, wherein the solvent is one of toluene and dimethyl formamide.

18. The compound according to claim 4, wherein R is one of a methyl, an ethyl, an isoamyl, and a benzyl, and wherein each of $R_1$ and $R_2$ is, independently, a methyl.

19. A method of preparing a compound of Formula VII,

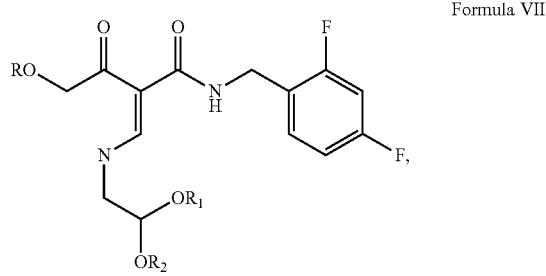

Formula VII comprising reacting a compound of Formula V with a compound of Formula VI,

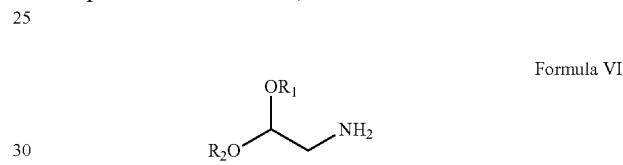

Formula VI to produce the compound of Formula VII, wherein each of $R_1$ and $R_2$ is, independently, an alkyl.

20. The method of claim 19, wherein the reaction of the compound of Formula V with the compound of Formula VI carried out in the presence of a solvent selected from one of an alcohol, an ether, a hydrocarbon, an amide, and mixtures thereof.

21. The method of claim 20, wherein the solvent is one of toluene and dimethyl formamide.

* * * * *